United States Patent
Honold et al.

(10) Patent No.: US 7,163,941 B2
(45) Date of Patent: Jan. 16, 2007

(54) PYRIDO[2,3-D]PYRIMIDIN-7-CARBOXYLIC ACID DERIVATIVES, THEIR MANUFACTURE AND USE AS PHARMACEUTICAL AGENTS

(75) Inventors: Konrad Honold, Penzberg (DE); Wolfgang Schaefer, Mannheim (DE); Stefan Scheiblich, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 131 days.

(21) Appl. No.: 10/809,067

(22) Filed: Mar. 25, 2004

(65) Prior Publication Data
US 2005/0130984 A1 Jun. 16, 2005

(30) Foreign Application Priority Data
Mar. 28, 2003 (EP) .................................. 03007182

(51) Int. Cl.
C07D 471/04 (2006.01)
A61K 31/495 (2006.01)
C07D 239/00 (2006.01)

(52) U.S. Cl. .............................. 514/235.8; 514/252.16; 514/264.11; 544/122; 544/279

(58) Field of Classification Search ................. 544/122, 544/279; 514/235.8, 252.16, 264.11
See application file for complete search history.

(56) References Cited

U.S. PATENT DOCUMENTS
5,733,913 A  3/1998 Blankley et al.

FOREIGN PATENT DOCUMENTS
WO  WO 96/15128   5/1996
WO  WO 155 147    2/2001
WO  WO 02/080360  10/2002
WO  WO 02/090360 A1  11/2002
WO  WO 03/000011  1/2003

OTHER PUBLICATIONS

Simone, Oncology: Introduction, Cecil Textbook of Medicine, 20th Edition, vol. 1, pp. 1004-1010, 1996.*
Traxler, Protein Tyrosine Kinase Inhibitors in Cancer Treatment, Exp. Opin. Ther. Patents, 7(6):571-588, 1997.*

* cited by examiner

*Primary Examiner*—Deepak Rao
(74) *Attorney, Agent, or Firm*—George W. Johnston; Patricia S. Rocha-Tramaloni; Brian C. Remy

(57) ABSTRACT

The invention describes compounds of the general formula I

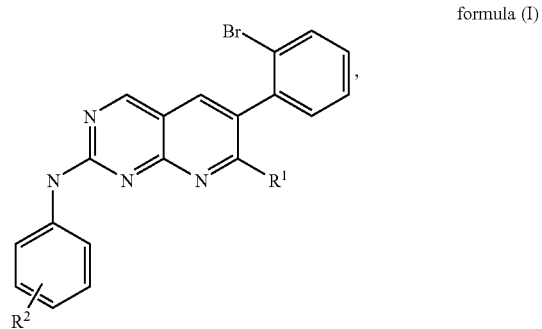

formula (I)

a process for their manufacture, medicaments containing them and their manufacture as well as the use of these compounds as pharmaceutically active agents. The compounds show activity as protein kinase inhibitors, in particular src family tyrosine kinase inhibitors, and may therefore be useful for the treatment of diseases mediated by said tyrosine kinases.

41 Claims, No Drawings

PYRIDO[2,3-D]PYRIMIDIN-7-CARBOXYLIC ACID DERIVATIVES, THEIR MANUFACTURE AND USE AS PHARMACEUTICAL AGENTS

BACKGROUND OF THE INVENTION

The present invention relates to novel, bicyclic pyrido[2,3-d]pyrimidines, to a process for their manufacture, medicaments containing them and their manufacture as well as the use of these compounds as pharmaceutically active agents.

Some substituted bicyclic nitrogen heterocycles are known in the art for their protein kinase, as well as their tyrosine kinase inhibitory activity. WO 02/090360 discloses pyrido[2,3-d]pyrimidines useful as kinase enzyme inhibitors and for the treatment of hyperproliferative diseases.

WO 03/000011 discloses phosphorus-containing derivatives of pyrido[2,3-d]pyrimidine as protein kinase inhibitors and for the treatment of bone disorders, cancer and signaling disorders in general.

WO 96/15128 discloses 6-aryl-pyrido[2,3-d]pyrimidines as inhibitors of protein tyrosine kinases and for the treatment of atherosclerosis, restenosis, psoriasis, bacterial infections and cancer.

Despite the progress documented in the above-mentioned literature, there remains a need for new compounds with an improved therapeutic index, such as improved activity, tolerability, selectivity or stability to name only a few.

SUMMARY OF THE INVENTION

The present invention relates to compounds of the general formula

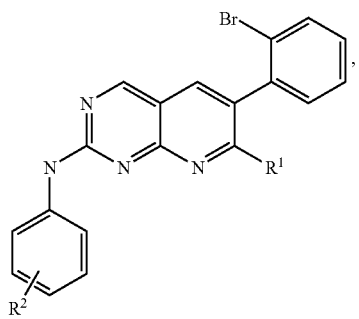

formula (I)

wherein
R¹ and R² are as described herewithin below.

The compounds according to this invention show activity as protein kinase inhibitors, in particular src family tyrosine kinase inhibitors, and may therefore be useful for the treatment of diseases mediated by said tyrosine kinases. The family of tyrosine kinases plays an important role in the regulation of cell signaling and cell proliferation by phosphorylating tyrosine residues of peptides and proteins. Inappropriate activation of tyrosine kinases is known to be involved in a variety of disease states including inflammatory, immunological, CNS disorders, or oncological disorders, or bone diseases. See for example Susa, M., et al., Trends Pharmacol. Sci., 21 (2000) 489–495; Biscardi, J. S., et al., Adv. Cancer Res. 76 (2000) 61–119.

Compounds of the present invention may be used as active agents in the prevention and therapy of, for example, transplant rejection, inflammatory bowel syndrome, rheumatoid arthritis, psoriasis, restenosis, allergic asthma, Alzheimers disease, Parkinson, stroke, osteoporosis, cancer, and benign hyperplasias.

The compounds of the present invention have surprisingly been found to show improved metabolic stability and/or selectivity, together with at least the same activity against src-tyrosine kinase compared to compounds known in the art.

Objects of the present invention are the compounds of formula I and pharmaceutically acceptable salts and their enantiomeric forms, the preparation of the above-mentioned compounds, medicaments containing them and their manufacture as well as the methods for using the above-mentioned compounds in the control or prevention of illnesses, especially of illnesses and disorders as mentioned above or in the manufacture of corresponding medicaments.

DETAILED DESCRIPTION OF THE INVENTION

The present derivatives are new compounds of the general formula

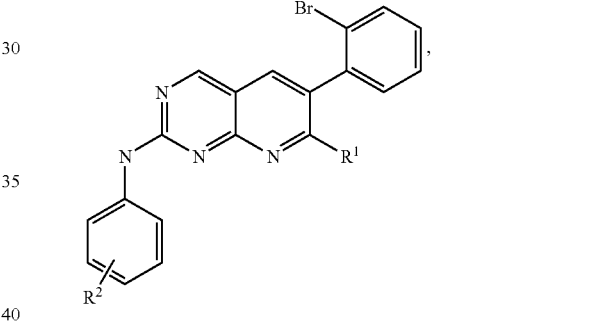

formula (I)

wherein
R¹ is —C(O)—NH-alkyl or —C(O)—N(alkyl)₂, which alkyl groups are unsubstituted or substituted with at least one substituent selected from
—OH;
—NH(alkyl);
—N(alkyl)₂;
—NH—C(O)-alkyl;
—C(O)—NH-alkyl;
—C(O)—N(alkyl)₂;
—C(O)—NH₂;
—O-alkyl;
-heterocyclyl;
—NH-heterocyclyl;
—NH—S(O)₂-alkyl;
—S(O)₂—NH₂; and
—S(O)-alkyl,
wherein when said at least one substituent contains an alkyl group, the alkyl group is unsubstituted or substituted with —OH;
or a group
—CN;
—C(O)—NH₂;
—C(O)—NH-heterocyclyl;
—C(O)—NH—NH—C(O)—NH₂; or —C(O)—NH—NH—C(O)-alkyl, which alkyl is unsubstituted or substituted with
—NH(alkyl); or
—N(alkyl)$_2$; and
R$^2$ is halogen;
heterocyclyl;
alkyl;
—NH—C(O)-alkyl;
—NH—S(O)$_2$-alkyl;
—(CH$_2$)$_m$—S(O)$_2$—NH$_2$;
—(CH$_2$)$_m$—S(O)$_2$—N(alkyl)$_2$;
—(CH$_2$)$_m$—S(O)$_2$—NH-(alkyl);
—O-alkyl; or
—S(O)$_n$-alkyl,
wherein when R2 contains an alkyl group, the alkyl group is unsubstituted or substituted by
—OH;
—O-alkyl;
—NH-alkyl; or
—N(alkyl)$_2$;
m is 0, 1, 2, 3, 4, 5 or 6;
n is 0, 1 or 2;

and pharmaceutically acceptable salts thereof.

Especially preferred are the compounds of formula I, wherein
R$^1$ is —C(O)—NH-alkyl or —C(O)—N(alkyl)$_2$, which alkyl groups are unsubstituted or substituted with
—OH;
—NH(alkyl);
—N(alkyl)$_2$;
—NH—C(O)-alkyl;
—C(O)—NH-alkyl;
—C(O)—N(alkyl)$_2$;
—C(O)—NH$_2$;
—O-alkyl;
-heterocyclyl;
—NH-heterocyclyl;
—S(O)$_2$—NH$_2$; or
—S(O)-alkyl,
wherein when R$^1$ contains an alkyl group, the alkyl group is unsubstituted or substituted with —OH;
or a group
—CN;
—C(O)—NH$_2$;
—C(O)—NH-heterocyclyl;
—C(O)—NH—NH—C(O)—NH$_2$; or
—C(O)—NH—NH—C(O)-alkyl, which alkyl is unsubstituted or substituted with
—NH(alkyl); or
—N(alkyl)$_2$; and
R$^2$ is halogen;
heterocyclyl;
—(CH$_2$)$_m$—S(O)$_2$—NH$_2$;
—(CH$_2$)$_m$—S(O)$_2$—N(alkyl)$_2$; or
—(CH$_2$)$_m$—S(O)$_2$—NH-(alkyl);
—O-alkyl; or
—S(O)$_n$-alkyl,
wherein when the R2 contains an alkyl group, the alkyl group is unsubstituted or substituted by
—OH;
—O—(C$_1$–C$_4$)alkyl;
—NH-alkyl; or
—N(alkyl)$_2$;
m is 0, 1, 2, 3, 4, 5 or 6;
n is 0, 1 or 2;

and pharmaceutically acceptable salts thereof.

As used herein, the term "alkyl" means a saturated, straight-chain or branched-chain hydrocarbon containing from 1 to 6, preferably from 1 to 4, carbon atoms, such as methyl, ethyl, n-propyl, isopropyl, n-butyl, 2-butyl, t-butyl, n-pentyl, n-hexyl as well as their isomers. "Substituted" alkyl groups are alkyl groups as defined above, which are once or, if possible, twice substituted. The substitution can occur at one or more positions and that the substituents at each substitution site are independently selected from the specified options.

As used herein, the term "(C$_1$–C$_4$)alkyl" means a saturated, straight-chain or branched-chain hydrocarbon containing from 1 to 4 carbon atoms, such as methyl, ethyl, n-propyl, isopropyl, n-butyl, 2-butyl, t-butyl.

The term "heterocyclyl" as used herein means a 5 to 8 membered, mono- or bicyclic, aromatic or non-aromatic hydrocarbon, wherein 1 to 3, preferably 1 or 2, carbon atoms are replaced by a nitrogen-, oxygen- or sulphor atom. Said heterocyclyl group is optionally substituted once or several times with alkyl, oxo or —C(O)—NH$_2$. Examples are 2-oxo-imidazolidin-1-yl; pyrrolidin-2-yl; pyrrolidin-3-yl; 2-oxo-pyrrolidin-1-yl; 1-methyl-pyrrolidin-2-yl; imidazol-4-yl; pyrazol-3-yl; 2-methyl-pyrazol-3-yl; 1-methyl-pyrazol-5-yl; 1,5-dimethyl-pyrazol-3-yl; 4-carbamoyl-pyrazol-3-yl; piperidin-3-yl; piperidin-4-yl; 1-methyl-piperidin-4-yl; morpholin-4-yl; pyridin-2-yl, 1-aza-bicyclo [2.2.2]oct-3-yl; [1,2,3]triazol-1-yl or 1-methyl-piperazine-4-yl.

The term "effective amount" or "therapeutically effective amount" means an amount of at least one compound of the invention, or a pharmaceutically acceptable salt thereof, that significantly mediates an inappropriate activation of src family tyrosine kinases.

The term "pharmaceutically acceptable," such as pharmaceutically acceptable carrier, excipient, adjuvant etc., means pharmacologically acceptable and substantially non-toxic to the patient to which the particular compound is administered.

Preferably the substituent R$^2$ in formula I is located in para or meta position.

When R$^2$ in formula I is a heterocyclus as defined above, said heterocyclus is either preferably located in para or meta position of the phenyl ring as mentioned above, or it is fused to the phenyl ring to form a bicyclic group. When the heterocyclus in R$^2$ is fused to the phenyl ring, said heterocyclus alone represents preferably a 5 or 6 membered, non-aromatic ring wherein one or two atoms are independently selected form oxygen, sulfur or a group —S(O)$_2$— and the remaining atoms being carbon atoms. Examples of such bicyclic groups, thus including the phenyl moiety to which R$^2$ is attached, are: 4,4-dioxo-3,4-dihydro-benzo[1,4] oxathiinyl; or 3-hydroxymethyl-2,3-dihydro-benzo[1,4]-dioxinyl.

An embodiment of the invention are the compounds of formula I, wherein
R$^1$ has the significance given above, and
R$^2$ is halogen;

and pharmaceutically acceptable salts thereof.

Another embodiment of the invention are the compounds of formula I, wherein
R$^1$ has the significance given above, and
R$^2$ is morpholin-4-yl;
—S-alkyl; or a group
—O-alkyl, which alkyl group is substituted with
—N(alkyl)$_2$;

and pharmaceutically acceptable salts thereof.

Such compounds are for example:
6-(2-Bromo-phenyl)-2-(3-methylsulfanyl-phenylamino)-pyrido[2,3-d]pyrimidine-7-carboxylic acid ((S)-pyrrolidin-2-ylmethyl)-amide,
6-(2-Bromo-phenyl)-2-(4-morpholin-4-yl-phenylamino)-pyrido[2,3-d]pyrimidine-7-carboxylic acid ((S)-pyrrolidin-2-ylmethyl)-amide,
6-(2-Bromo-phenyl)-2-(4-morpholin-4-yl-phenylamino)-pyrido[2,3-d]pyrimidine-7-carboxylic acid ((R)-pyrrolidin-2-ylmethyl)-amide, or
6-(2-Bromo-phenyl)-2-(4-morpholin-4-yl-phenylamino)-pyrido[2,3-d]pyrimidine-7-carboxylic acid (2-[1,2,3]triazol-1-yl-ethyl)-amide.

Another embodiment of the invention are the compounds of formula I, wherein
$R^1$ is —C(O)—NH-alkyl, which alkyl group is substituted with
—OH;
—NH(alkyl);
—N(alkyl)$_2$; or
—S(O)$_2$—NH$_2$;
or a group
—C(O)—NH-piperidin-3-yl;
—C(O)—NH-pyrrolidin-3-yl;
—C(O)—NH—CH$_2$-pyrrolidin-2-yl; or
—C(O)—NH—(CH$_2$)$_2$-imidazol-4-yl; and
$R^2$ is morpholin-4-yl;
—S-alkyl;
—O-alkyl, which alkyl group is substituted with
—N(alkyl)$_2$; or
—S(O)$_2$—NH-alkyl, which alkyl group is substituted with
—OH; or
—O—(C$_1$–C$_4$)alkyl;

and pharmaceutically acceptable salts thereof.
Such compounds are for example:
6-(2-Bromo-phenyl)-2-(4-morpholin-4-yl-phenylamino)-pyrido[2,3-d]pyrimidine-7-carboxylic acid[2-(3H-imidazol-4-yl)-ethyl]-amide,
6-(2-Bromo-phenyl)-2-(4-morpholin-4-yl-phenylamino)-pyrido[2,3-d]pyrimidine-7-carboxylic acid (S)-piperidin-3-ylamide,
6-(2-Bromo-phenyl)-2-(3-methylsulfanyl-phenylamino)-pyrido[2,3-d]pyrimidine-7-carboxylic acid (S)-piperidin-3-ylamide,
6-(2-Bromo-phenyl)-2-(4-morpholin-4-yl-phenylamino)-pyrido[2,3-d]pyrimidine-7-carboxylic acid (2-sulfamoyl-ethyl)-amide,
6-(2-Bromo-phenyl)-2-(3-methylsulfanyl-phenylamino)-pyrido[2,3-d]pyrimidine-7-carboxylic acid (2-sulfamoyl-ethyl)-amide, or
6-(2-Bromo-phenyl)-2-(4-morpholin-4-yl-phenylamino)-pyrido[2,3-d]pyrimidine-7-carboxylic acid (2-hydroxy-ethyl)-amide.

Preferred are the compounds of formula I, wherein
$R^1$ is —C(O)—NH-alkyl, which alkyl group is substituted with
—OH;
—NH(alkyl);
—N(alkyl)$_2$; or
—S(O)$_2$—NH$_2$; and
$R^2$ is morpholin-4-yl;

and pharmaceutically acceptable salts thereof.
Also preferred are the compounds of formula I, wherein
$R^1$ is —C(O)—NH-alkyl, which alkyl group is substituted with
—OH;
—NH(alkyl);
—N(alkyl)$_2$; or
—S(O)$_2$—NH$_2$; and
$R^2$ is —S-alkyl;

and pharmaceutically acceptable salts thereof.
Also preferred are the compounds of formula I, wherein
$R^1$ is —C(O)—NH-alkyl, which alkyl group is substituted with
—OH;
—NH(alkyl);
—N(alkyl)$_2$; or
—S(O)$_2$—NH$_2$; and
$R^2$ is —O-alkyl, which alkyl group is substituted with
—N(alkyl)$_2$;

and pharmaceutically acceptable salts thereof.
Also preferred are the compounds of formula I, wherein
$R^1$ is —C(O)—NH-alkyl, which alkyl group is substituted with
—OH;
—NH(alkyl);
—N(alkyl)$_2$; or
—S(O)$_2$—NH$_2$; and
$R^2$ is —S(O)$_2$—NH-alkyl, which alkyl group is substituted with
—OH; or
—O—(C$_1$–C$_4$)alkyl;

and pharmaceutically acceptable salts thereof.
Further preferred are the compounds of formula I, wherein
$R^1$ is —C(O)—NH-piperidin-3-yl;
—C(O)—NH-pyrrolidin-3-yl;
—C(O)—NH—CH$_2$-pyrrolidin-2-yl; or
—C(O)—NH—(CH$_2$)$_2$-imidazol-4-yl; and
$R^2$ is morpholin-4-yl;

and pharmaceutically acceptable salts thereof.
Further preferred are the compounds of formula I, wherein
$R^1$ is —C(O)—NH-piperidin-3-yl;
—C(O)—NH-pyrrolidin-3-yl;
—C(O)—NH—CH$_2$-pyrrolidin-2-yl; or
—C(O)—NH—(CH$_2$)$_2$-imidazol-4-yl; and
$R^2$ is —S-alkyl;

and pharmaceutically acceptable salts thereof.
Further preferred are the compounds of formula I, wherein
$R^1$ is —C(O)—NH-piperidin-3-yl;
—C(O)—NH-pyrrolidin-3-yl;
—C(O)—NH—CH$_2$-pyrrolidin-2-yl; or
—C(O)—NH—(CH$_2$)$_2$-imidazol-4-yl; and
$R^2$ is —O-alkyl, which alkyl group is substituted with
—N(alkyl)$_2$;

and pharmaceutically acceptable salts thereof.
Further preferred are the compounds of formula I, wherein
$R^1$ is —C(O)—NH-piperidin-3-yl;
—C(O)—NH-pyrrolidin-3-yl;
—C(O)—NH—CH$_2$-pyrrolidin-2-yl; or
—C(O)—NH—(CH$_2$)$_2$-imidazol-4-yl; and
$R^2$ is —S(O)$_2$—NH-alkyl, which alkyl group is substituted with
—OH; or
—O—(C$_1$–C$_4$)alkyl;

and pharmaceutically acceptable salts thereof.

Further preferred are the compounds of formula I, wherein
$R^1$ is —CN;
$R^2$ is morpholin-4-yl;
—S-alkyl;
—O-alkyl, which alkyl group is substituted with
—N(alkyl)$_2$; or
—S(O)$_2$—NH-alkyl, which alkyl group is substituted with
—OH; or
—O—(C$_1$–C$_4$)alkyl;

and pharmaceutically acceptable salts thereof.

Still another embodiment of the invention are the compounds of formula I, wherein
$R^1$ is —C(O)—NH-alkyl, which alkyl group is optionally substituted with
—OH;
—NH(alkyl);
—N(alkyl)$_2$;
—NH—C(O)-alkyl;
—C(O)—NH-alkyl;
—C(O)—N(alkyl)$_2$;
—C(O)—NH$_2$;
—O-alkyl;
—S(O)-alkyl, which alkyl is optionally substituted with
—OH; or
—S(O)$_2$—NH$_2$; and
$R^2$ is halogen;

and pharmaceutically acceptable salts thereof.

Such compounds are for example:
6-(2-Bromo-phenyl)-2-(4-fluoro-phenylamino)-pyrido[2,3-d]pyrimidine-7-carboxylic acid (2-dimethylamino-ethyl)-amide;
6-(2-Bromo-phenyl)-2-(4-fluoro-phenylamino)-pyrido[2,3-d]pyrimidine-7-carboxylic acid (2-methoxy-ethyl)-amide;
6-(2-Bromo-phenyl)-2-(4-fluoro-phenylamino)-pyrido[2,3-d]pyrimidine-7-carboxylic acid (3-dimethylamino-propyl)-amide;
6-(2-Bromo-phenyl)-2-(4-fluoro-phenylamino)-pyrido[2,3-d]pyrimidine-7-carboxylic acid (3-dimethylamino-2,2-dimethyl-propyl)-amide;
6-(2-Bromo-phenyl)-2-(4-fluoro-phenylamino)-pyrido[2,3-d]pyrimidine-7-carboxylic acid (2-acetylamino-ethyl)-amide;
6-(2-Bromo-phenyl)-2-(4-fluoro-phenylamino)-pyrido[2,3-d]pyrimidine-7-carboxylic acid (2-methylamino-ethyl)-amide;
6-(2-Bromo-phenyl)-2-(4-fluoro-phenylamino)-pyrido[2,3-d]pyrimidine-7-carboxylic acid carbamoylmethyl-amide;
6-(2-Bromo-phenyl)-2-(4-fluoro-phenylamino)-pyrido[2,3-d]pyrimidine-7-carboxylic acid (2-dimethylamino-1-methyl-ethyl)-amide;
6-(2-Bromo-phenyl)-2-(4-fluoro-phenylamino)-pyrido[2,3-d]pyrimidine-7-carboxylic acid methylcarbamoylmethyl-amide;
6-(2-Bromo-phenyl)-2-(4-fluoro-phenylamino)-pyrido[2,3-d]pyrimidine-7-carboxylic acid (2-dimethylamino-propyl)-amide;
6-(2-Bromo-phenyl)-2-(4-fluoro-phenylamino)-pyrido[2,3-d]pyrimidine-7-carboxylic acid dimethylcarbamoylmethyl-amide;
6-(2-Bromo-phenyl)-2-(4-fluoro-phenylamino)-pyrido[2,3-d]pyrimidine-7-carboxylic acid (3-methylamino-propyl)-amide;
6-(2-Bromo-phenyl)-2-(4-fluoro-phenylamino)-pyrido[2,3-d]pyrimidine-7-carboxylic acid (2-sulfamoyl-ethyl)-amide;
6-(2-Bromo-phenyl)-2-(4-fluoro-phenylamino)-pyrido[2,3-d]pyrimidine-7-carboxylic acid (2-hydroxy-ethyl)-amide;
6-(2-Bromo-phenyl)-2-(4-fluoro-phenylamino)-pyrido[2,3-d]pyrimidine-7-carboxylic acid (3-hydroxy-propyl)-amide;
(S)-6-(2-Bromo-phenyl)-2-(4-fluoro-phenylamino)-pyrido[2,3-d]pyrimidine-7-carboxylic acid (2,3-dihydroxy-propyl)-amide;
(R)-6-(2-Bromo-phenyl)-2-(4-fluoro-phenylamino)-pyrido[2,3-d]pyrimidine-7-carboxylic acid (2,3-dihydroxy-propyl)-amide
6-(2-Bromo-phenyl)-2-(4-fluoro-phenylamino)-pyrido[2,3-d]pyrimidine-7-carboxylic acid (2-methanesulfinyl-ethyl)-amide; or
6-(2-Bromo-phenyl)-2-(4-fluoro-phenylamino)-pyrido[2,3-d]pyrimidine-7-carboxylic acid [2-(2-hydroxy-ethanesulfinyl)-ethyl]-amide.

Yet another embodiment of the invention are the compounds of formula I, wherein
$R^1$ is —C(O)—N(CH$_3$)alkyl, which alkyl group is optionally substituted with
—NH(alkyl);
—N(alkyl)$_2$; and
$R^2$ is halogen;

and pharmaceutically acceptable salts thereof.

Such a compound is for example:
6-(2-Bromo-phenyl)-2-(4-fluoro-phenylamino)-pyrido[2,3-d]pyrimidine-7-carboxylic acid (2-dimethylamino-ethyl)-methyl-amide.

Yet another embodiment of the invention are the compounds of formula I, wherein
$R^1$ is —C(O)—NH-alkyl, which alkyl group is substituted with
morpholin-4-yl;
pyrrolidinyl;
2-oxo-imidazolidinyl;
2-oxo-pyrrolidinyl;
1-methyl-pyrrolidinyl;
3H-imidazolyl;
1,5-dimethyl-pyrazolyl; or
—NH-pyridinyl;
$R^2$ is halogen;

and pharmaceutically acceptable salts thereof.

Such compounds are for example:
6-(2-Bromo-phenyl)-2-(4-fluoro-phenylamino)-pyrido[2,3-d]pyrimidine-7-carboxylic acid (2-morpholin-4-yl-ethyl)-amide;
6-(2-Bromo-phenyl)-2-(4-fluoro-phenylamino)-pyrido[2,3-d]pyrimidine-7-carboxylic acid [2-(2-oxo-imidazolidin-1-yl)-ethyl]-amide;
(R)-6-(2-Bromo-phenyl)-2-(4-fluoro-phenylamino)-pyrido[2,3-d]pyrimidine-7-carboxylic acid (pyrrolidin-2-ylmethyl)-amide;
6-(2-Bromo-phenyl)-2-(4-fluoro-phenylamino)-pyrido[2,3-d]pyrimidine-7-carboxylic acid [3-(2-oxo-pyrrolidin-1-yl)-propyl]-amide;
6-(2-Bromo-phenyl)-2-(4-fluoro-phenylamino)-pyrido[2,3-d]pyrimidine-7-carboxylic acid (3-morpholin-4-yl-propyl)-amide;
6-(2-Bromo-phenyl)-2-(4-fluoro-phenylamino)-pyrido[2,3-d]pyrimidine-7-carboxylic acid [2-(1-methyl-pyrrolidin-2-yl)-ethyl]-amide;

6-(2-Bromo-phenyl)-2-(4-fluoro-phenylamino)-pyrido[2,3-d]pyrimidine-7-carboxylic acid [2-(pyridin-2-ylamino)-ethyl]-amide;

6-(2-Bromo-phenyl)-2-(4-fluoro-phenylamino)-pyrido[2,3-d]pyrimidine-7-carboxylic acid [2-(3H-imidazol-4-yl)-ethyl]-amide;

6-(2-Bromo-phenyl)-2-(4-fluoro-phenylamino)-pyrido[2,3-d]pyrimidine-7-carboxylic acid (1,5-dimethyl-1H-pyrazol-3-ylmethyl)-amide; or 6-(2-Bromo-phenyl)-2-(4-fluoro-phenylamino)-pyrido[2,3-d]pyrimidine-7-carboxylic acid ((S)-pyrrolidin-2-ylmethyl)-amide.

Yet another embodiment of the invention are the compounds of formula I, wherein $R^1$ is —C(O)—NH-alkyl, which alkyl group is substituted with
—NH-alkyl;
—N(alkyl)$_2$; or
—C(O)—NH-piperidin-4-yl; and $R^2$ is morpholin-4-yl;
—S-alkyl; or
—O-alkyl, which alkyl group is substituted with
—N(alkyl)$_2$;

and pharmaceutically acceptable salts thereof.

Such compounds are for example:

6-(2-Bromo-phenyl)-2-(3-methylsulfanyl-phenylamino)-pyrido[2,3-d]pyrimidine-7-carboxylic acid (2-dimethylamino-ethyl)-amide;

6-(2-Bromo-phenyl)-2-(4-morpholin-4-yl-phenylamino)-pyrido[2,3-d]pyrimidine-7-carboxylic acid (2-dimethylamino-ethyl)-amide;

6-(2-Bromo-phenyl)-2-(4-morpholin-4-yl-phenylamino)-pyrido[2,3-d]pyrimidine-7-carboxylic acid (2-methylamino-ethyl)-amide;

6-(2-Bromo-phenyl)-2-[4-(2-diethylamino-ethoxy)-phenylamino]-pyrido[2,3-d]pyrimidine-7-carboxylic acid (2-dimethylamino-ethyl)-amide;

6-(2-Bromo-phenyl)-2-(4-morpholin-4-yl-phenylamino)-pyrido[2,3-d]pyrimidine-7-carboxylic acid piperidin-4-ylamide; or 6-(2-Bromo-phenyl)-2-(3-methylsulfanyl-phenylamino)-pyrido[2,3-d]pyrimidine-7-carboxylic acid (2-methylamino-ethyl)-amide.

Yet another embodiment of the invention are the compounds of formula I, wherein $R^1$ is —C(O)—NH-heterocyclyl;
—C(O)—NH—NH—C(O)—NH$_2$; or
—C(O)—NH—NH—C(O)-alkyl, which alkyl is optionally substituted with
—NH(alkyl); or
—N(alkyl)$_2$;

$R^2$ is halogen;

and pharmaceutically acceptable salts thereof.

Such compounds are for example:

(R)-6-(2-Bromo-phenyl)-2-(4-fluoro-phenylamino)-pyrido[2,3-d]pyrimidine-7-carboxylic acid piperidin-3-ylamide;

(S)-6-(2-Bromo-phenyl)-2-(4-fluoro-phenylamino)-pyrido[2,3-d]pyrimidine-7-carboxylic acid piperidin-3-ylamide;

6-(2-Bromo-phenyl)-2-(4-fluoro-phenylamino)-pyrido[2,3-d]pyrimidine-7-carboxylic acid piperidin-4-ylamide;

1-[6-(2-Bromo-phenyl)-2-(4-fluoro-phenylamino)-pyrido[2,3-d]pyrimidine-7-carbonyl]semicarbazide;

6-(2-Bromo-phenyl)-2-(4-fluoro-phenylamino)-pyrido[2,3-d]pyrimidine-7-carboxylic acid N'-(2-dimethylamino-acetyl)-hydrazide;

6-(2-Bromo-phenyl)-2-(4-fluoro-phenylamino)-pyrido[2,3-d]pyrimidine-7-carboxylic acid (1-methyl-piperidin-4-yl)-amide;

(S)-6-(2-Bromo-phenyl)-2-(4-fluoro-phenylamino)-pyrido[2,3-d]pyrimidine-7-carboxylic acid pyrrolidin-3-ylamide;

(R)-6-(2-Bromo-phenyl)-2-(4-fluoro-phenylamino)-pyrido[2,3-d]pyrimidine-7-carboxylic acid pyrrolidin-3-ylamide;

6-(2-Bromo-phenyl)-2-(4-fluoro-phenylamino)-pyrido[2,3-d]pyrimidine-7-carboxylic acid (1-aza-bicyclo[2.2.2]oct-3-yl)-amide;

6-(2-Bromo-phenyl)-2-(4-fluoro-phenylamino)-pyrido[2,3-d]pyrimidine-7-carboxylic acid (1H-pyrazol-3-yl)-amide;

6-(2-Bromo-phenyl)-2-(4-fluoro-phenylamino)-pyrido[2,3-d]pyrimidine-7-carboxylic acid (2-methyl-2H-pyrazol-3-yl)-amide; or 6-(2-Bromo-phenyl)-2-(4-fluoro-phenylamino)-pyrido[2,3-d]pyrimidine-7-carboxylic acid (4-carbamoyl-1H-pyrazol-3-yl)-amide.

Yet another embodiment of the invention are the compounds of formula I, wherein $R^1$ is —C(O)—NH$_2$; and $R^2$ is morpholin-4-yl;
—(CH$_2$)$_m$—S(O)$_2$—NH-(alkyl);
—(CH$_2$)$_m$—S(O)$_2$—NH$_2$; or a group
—O-alkyl, —S(O)$_n$-alkyl, which alkyl groups are optionally substituted by
—OH;
—NH-alkyl; or
—N(alkyl)$_2$;

m is 0, 1, 2, 3, 4, 5 or 6;

n is 0, 1 or 2;

and pharmaceutically acceptable salts thereof.

Such compounds are for example:

6-(2-Bromo-phenyl)-2-(4-morpholin-4-yl-phenylamino)-pyrido[2,3-d]pyrimidine-7-carboxylic acid amide;

6-(2-Bromo-phenyl)-2-[4-(2-diethylamino-ethoxy)-phenylamino]-pyrido[2,3-d]pyrimidine-7-carboxylic acid amide;

6-(2-Bromo-phenyl)-2-(3-methylsulfanyl-phenylamino)-pyrido[2,3-d]pyrimidine-7-carboxylic acid amide;

6-(2-Bromo-phenyl)-2-(4-sulfamoyl-phenylamino)-pyrido[2,3-d]pyrimidine-7-carboxylic acid amide;

6-(2-Bromo-phenyl)-2-(3-methylsulfamoylmethyl-phenylamino)-pyrido[2,3-d]pyrimidine-7-carboxylic acid amide;

6-(2-Bromo-phenyl)-2-[3-(2-hydroxy-ethanesulfonyl)-phenylamino]-pyrido[2,3-d]pyrimidine-7-carboxylic acid amide; or 6-(2-Bromo-phenyl)-2-(3-methanesulfonyl-phenylamino)-pyrido[2,3-d]pyrimidine-7-carboxylic acid amide.

Yet another embodiment of the invention are the compounds of formula I, wherein $R^1$ is —CN; and $R^2$ is morpholin-4-yl;
—S(O)$_n$-alkyl; or a group
—O-alkyl, which alkyl group is optionally substituted by
—OH;
—NH-alkyl;
—N(alkyl)$_2$;

n is 0, 1 or 2;

and pharmaceutically acceptable salts thereof.

Such compounds are for example:
6-(2-Bromo-phenyl)-2-(4-morpholin-4-yl-phenylamino)-pyrido[2,3-d]pyrimidine-7-carbonitrile; compound with trifluoro-acetic acid;
6-(2-Bromo-phenyl)-2-(3-methanesulfonyl-phenylamino)-pyrido[2,3-d]pyrimidine-7-carbonitrile;
6-(2-Bromo-phenyl)-2-[4-(2-diethylamino-ethoxy)-phenylamino]-pyrido[2,3-d]pyrimidine-7-carbonitrile;
6-(2-Bromo-phenyl)-2-[4-(2-hydroxy-ethoxy)-phenylamino]-pyrido[2,3-d]pyrimidine-7-carbonitrile;
6-(2-Bromo-phenyl)-2-[4-(2-ethylamino-ethoxy)-phenylamino]-pyrido[2,3-d]pyrimidine-7-carbonitrile;
6-(2-Bromo-phenyl)-2-(3-methanesulfinyl-phenylamino)-pyrido[2,3-d]pyrimidine-7-carbonitrile; or
6-(2-Bromo-phenyl)-2-[3-(2-hydroxy-ethanesulfonyl)-phenylamino]-pyrido[2,3-d]pyrimidine-7-carbonitrile.

Still another embodiment of the present invention are the compounds of formula I, wherein
$R^1$ is —C(O)—NH—(CH$_2$)$_2$—NH—S(O)$_2$—CH$_3$; and
$R^2$ is halogen;
　heterocyclyl;
　alkyl;
　—NH—C(O)-alkyl;
　—NH—S(O)$_2$-alkyl;
　—(CH$_2$)$_m$—S(O)$_2$—NH$_2$;
　—(CH$_2$)$_m$—S(O)$_2$—N(alkyl)$_2$;
　—(CH$_2$)$_m$—S(O)$_2$—NH-(alkyl);
　—O-alkyl; or
　—S(O)$_n$-alkyl, all alkyl groups being optionally substituted by
　　—OH;
　　—O-alkyl;
　　—NH-alkyl; or
　　—N(alkyl)$_2$;
m is 0, 1, 2, 3, 4, 5 or 6;
n is 0, 1 or 2;

and pharmaceutically acceptable salts thereof.
Such compounds are for example:
6-(2-Bromo-phenyl)-2-(4-morpholin-4-yl-phenylamino)-pyrido[2,3-d]pyrimidine-7-carboxylic acid (2-methanesulfonylamino-ethyl)-amide,
6-(2-Bromo-phenyl)-2-(3-methanesulfonylamino-phenylamino)-pyrido[2,3-d]pyrimidine-7-carboxylic acid (2-methanesulfonylamino-ethyl)-amide,
6-(2-Bromo-phenyl)-2-[4-(2-hydroxy-ethoxy)-phenylamino]-pyrido[2,3-d]pyrimidine-7-carboxylic acid (2-methanesulfonylamino-ethyl)-amide,
6-(2-Bromo-phenyl)-2-[4-(4-methyl-piperazin-1-yl)-phenylamino]-pyrido[2,3-d]pyrimidine-7-carboxylic acid (2-methanesulfonylamino-ethyl)-amide,
6-(2-Bromo-phenyl)-2-(3-methoxy-phenylamino)-pyrido[2,3-d]pyrimidine-7-carboxylic acid (2-methanesulfonylamino-ethyl)-amide,
2-(3-Acetylamino-phenylamino)-6-(2-bromo-phenyl)-pyrido[2,3-d]pyrimidine-7-carboxylic acid (2-methanesulfonylamino-ethyl)-amide,
6-(2-Bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (2-methanesulfonylamino-ethyl)-amide,
6-(2-Bromo-phenyl)-2-[3-(2-hydroxy-ethylsulfanyl)-phenylamino]-pyrido[2,3-d]pyrimidine-7-carboxylic acid (2-methanesulfonylamino-ethyl)-amide, or
6-(2-Bromo-phenyl)-2-(3-hydroxymethyl-2,3-dihydro-benzo[1,4]dioxin-6-ylamino)-pyrido[2,3-d]pyrimidine-7-carboxylic acid (2-methanesulfonylamino-ethyl)-amide.

Yet another embodiment of the present invention are the compounds:
6-(2-Bromo-phenyl)-2-(4-fluoro-phenylamino)-pyrido[2,3-d]pyrimidine-7-carboxylic acid (piperidin-2-ylmethyl)-amide,
6-(2-Bromo-phenyl)-2-(4-methanesulfinyl-phenylamino)-pyrido[2,3-d]pyrimidine-7-carboxylic acid (2-hydroxy-ethyl)-amide,
6-(2-Bromo-phenyl)-2-(3-methanesulfinyl-phenylamino)-pyrido[2,3-d]pyrimidine-7-carboxylic acid (2-hydroxy-ethyl)-amide,
6-(2-Bromo-phenyl)-2-[3-(2-hydroxy-ethylsulfamoyl)-phenylamino]-pyrido[2,3-d]pyrimidine-7-carboxylic acid (2-hydroxy-ethyl)-amide,
6-(2-Bromo-phenyl)-2-[4-(2-hydroxy-ethylsulfamoyl)-phenylamino]-pyrido[2,3-d]pyrimidine-7-carboxylic acid (2-hydroxy-ethyl)-amide,
6-(2-Bromo-phenyl)-2-(4-methanesulfinyl-phenylamino)-pyrido[2,3-d]pyrimidine-7-carboxylic acid (2-sulfamoyl-ethyl)-amide,
6-(2-Bromo-phenyl)-2-(3-methanesulfinyl-phenylamino)-pyrido[2,3-d]pyrimidine-7-carboxylic acid (2-sulfamoyl-ethyl)-amide,
6-(2-Bromo-phenyl)-2-[4-(2-hydroxy-ethoxy)-phenylamino]-pyrido[2,3-d]pyrimidine-7-carboxylic acid (2-sulfamoyl-ethyl)-amide, or
6-(2-Bromo-phenyl)-2-(3-methanesulfonyl-phenylamino)-pyrido[2,3-d]pyrimidine-7-carboxylic acid (2-sulfamoyl-ethyl)-amide.

Yet another embodiment of the present invention are the compounds of formula I wherein
$R^1$ is —C(O)—NH-alkyl, which alkyl group is substituted by
　—OH;
　—S(O)$_2$—NH$_2$;
　pyrrolidin-2-yl; and
$R^2$ is —NH—C(O)—CH$_3$;
　—NH—S(O)$_2$—CH$_3$;
　—CH$_2$—OH; or
　$R^2$ is fused to the phenyl ring to form a 4,4-dioxo-3,4-dihydro-2H-4lambda*6*-benzo[1,4]oxathiinyl moiety;

and pharmaceutically acceptable salts thereof.
Such compounds are for example:
6-(2-Bromo-phenyl)-2-(3-hydroxymethyl-phenylamino)-pyrido[2,3-d]pyrimidine-7-carboxylic acid (2-hydroxy-ethyl)-amide,
6-(2-Bromo-phenyl)-2-(3-hydroxymethyl-phenylamino)-pyrido[2,3-d]pyrimidine-7-carboxylic acid (2-sulfamoyl-ethyl)-amide,
6-(2-Bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (2-sulfamoyl-ethyl)-amide,
6-(2-Bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (pyrrolidin-2-ylmethyl)-amide HCl salt,
6-(2-Bromo-phenyl)-2-(3-methanesulfonylamino-phenylamino)-pyrido[2,3-d]pyrimidine-7-carboxylic acid (pyrrolidin-2-ylmethyl)-amide HCl salt, or
2-(3-Acetylamino-phenylamino)-6-(2-bromo-phenyl)-pyrido[2,3-d]pyrimidine-7-carboxylic acid (pyrrolidin-2-ylmethyl)-amide HCl salt.

Still another embodiment of the invention is a process for the manufacture of the compounds according to this invention, wherein (a) the sulfide group in the compounds of the general formula (II)

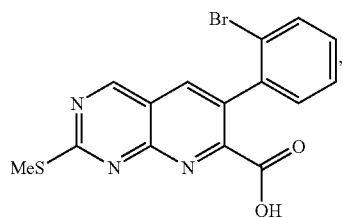

formula (II)

is converted into the corresponding sulfoxide group, which sulfoxide group is (b) substituted by the respective anilines of formula (II-A)

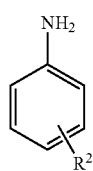

formula (II-A)

wherein $R^2$ has the meaning given herein before, to give the compounds of the general formula (IV)

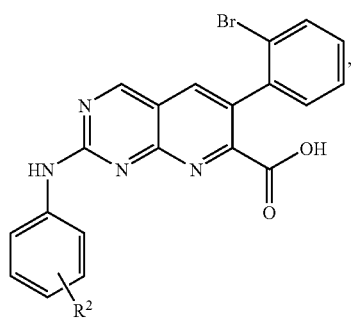

formula (IV)

(c) the —COOH group in formula (IV) is converted into an amide derivative of formula (I); and (d) if desired a primary amide derivative obtained from (c) is further converted into its corresponding 7-carbonitril derivative of formula (I); and (e) if desired said compound of the general formula (I), obtained from (c) or (d), is converted into a pharmaceutically acceptable salt.

In a more detailed description, the compounds of formula (I) wherein $R^1$ is attached via an amid group are represented by the general formula (Ia). Such compounds can be prepared from the carboxylic acids of formula (II), using standard reactions well known to the one skilled in the art. The synthesis of the compounds of the general formula (Ia) is shown in scheme 1, wherein $R^3$ has the significance given above for $R^1$ without the group —CN, therefore $R^3$ is —C(O)—NH-alkyl or —C(O)—N(alkyl)$_2$, which alkyl groups are optionally substituted with
—OH;
—NH(alkyl);
—N(alkyl)$_2$;
—NH—C(O)-alkyl;
—C(O)—NH-alkyl;
—C(O)—N(alkyl)$_2$;
—C(O)—NH$_2$;
—O-alkyl;
-heterocyclyl;
—NH-heterocyclyl;
—NH—S(O)$_2$-alkyl;
—S(O)$_2$—NH$_2$; or
—S(O)-alkyl, which alkyl is optionally substituted with —OH;
or a group
—C(O)—NH$_2$;
—C(O)—NH-heterocyclyl;
—C(O)—NH—NH—C(O)—NH$_2$; or
—C(O)—NH—NH—C(O)-alkyl, which alkyl is optionally substituted with
—NH(alkyl); or
—N(alkyl)$_2$;

and $R^2$ has the significance given above.

Scheme 1

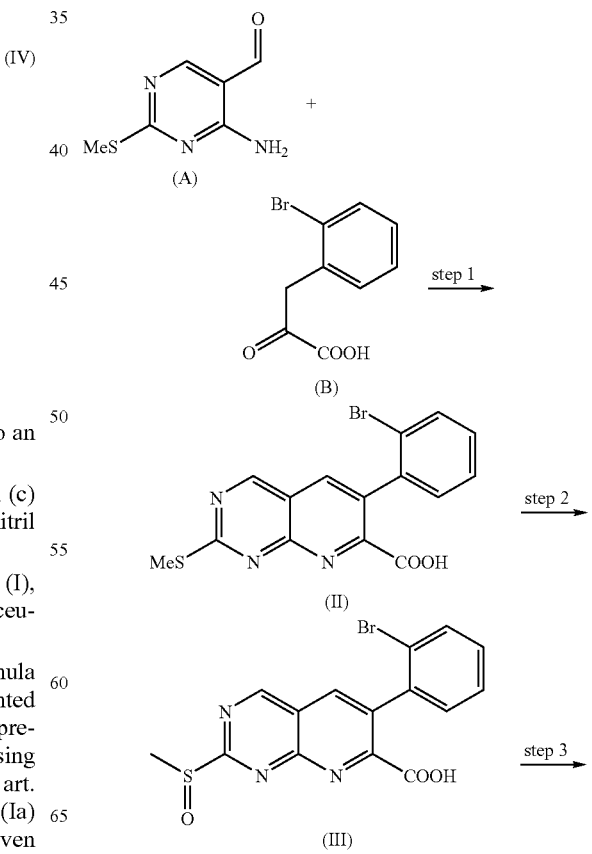

-continued

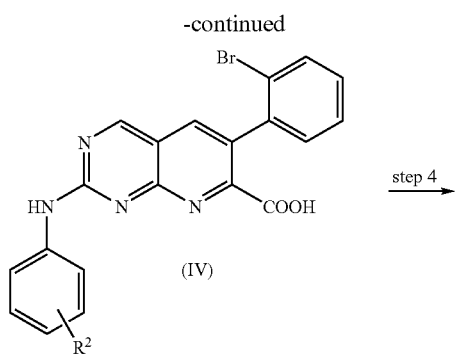

(IV)

step 4 →

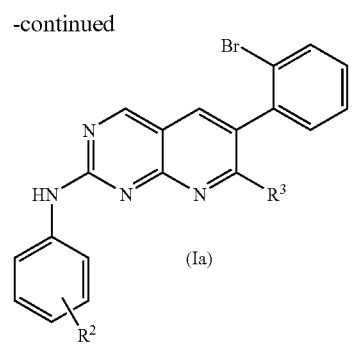

(Ia)

Primary carboxamides of the formulae (Ia) or (V), wherein R³ is —C(O)—NH₂, can be converted into nitriles of the general formula (Ib) by conventional methods, e.g. dehydration with SOCl₂ or POCl₃. Said nitrites of formula (Ib) may also be prepared from known pyridones (VII) according to scheme 3, wherein R² has the significance given herein before and L is a suitable leaving group.

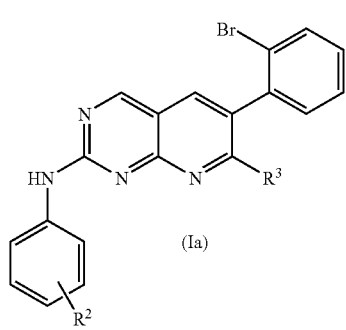

(Ia)

Alternatively, the carboxylic acids (II) can first be converted to carboxamides (V) and subsequently substituted by anilins on position 2 according to scheme 2, wherein R³ and R² have the significance given above.

Scheme 3

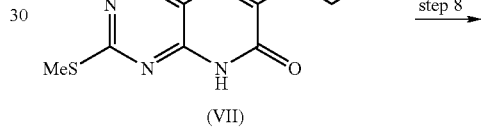

(VII)

step 8 →

Scheme 2

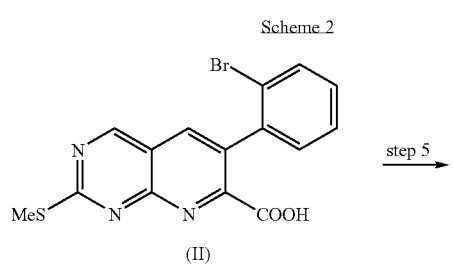

(II)

step 5 →

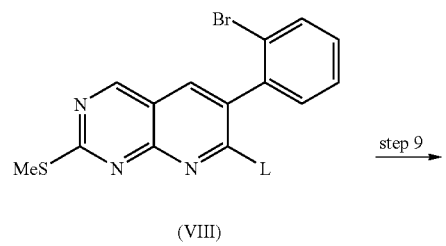

(VIII)

step 9 →

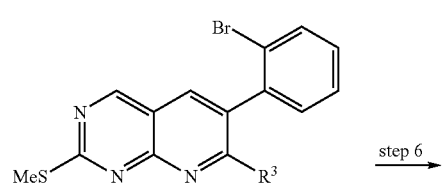

(V)

step 6 →

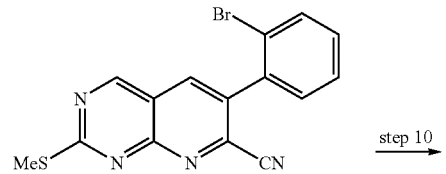

(IX)

step 10 →

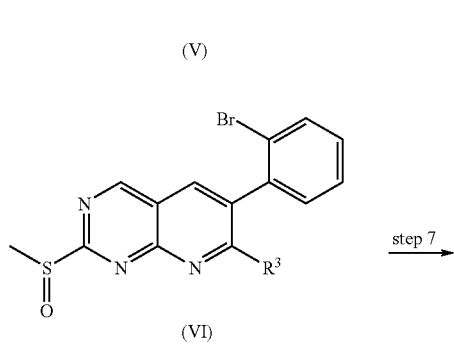

(VI)

step 7 →

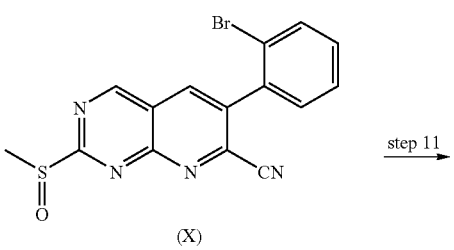

(X)

step 11 →

-continued

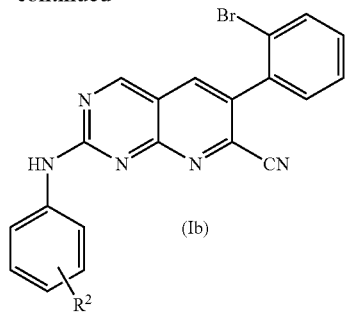

(Ib)

Step 1: 3-(2-bromo-phenyl)-pyruvic acid of formula (B), or in general arylpyruvic acids, can be condensed with a suitable pyrimidine carbaldehyde of formula (A) to give compound (II). Said condensation reaction can be performed under basic conditions, e.g with sodium hydroxide (NaOH) in water or methanol (MeOH) or 1,8-Diazabicyclo[5.4.0]undec-7-ene (DBU) or potassium tert-butoxylate (KOtBu) in dimethyl formamide (DMF), 1-Methyl-2-pyrrolidinone (NMP) or tetrahydrofuran (THF). Alternatively, the condensation reaction is performed in acetic acid in the presence of sodium acetate. Reaction temperatures range from room temperature (RT) to 150° C.

Steps 2, 6 and 10:

A methylthio or alternatively any other alkylthio or arylthio group on position 2 of the pyridopyrimidines of formulae (II), (V) or (IX) can be converted into a suitable leaving group by oxidation to the corresponding sulfone or sulfoxide of the formulae (III), (VI) or (X). Suitable reagents are for instance 3-Chloroperoxybenzoic acid (mCPBA) or 2-benzenesulfonyl-3-phenyl-oxaziridine in inert solvents like dichlormethane ($CH_2Cl_2$), chloroforme ($CHCl_3$), or MTBE at temperatures ranging from −40° C. to +65° C.

Steps 3, 7, and 11:

The sulfoxides or sulfones from steps 2, 6 or 10 can be reacted in purified form or as crude products with anilines to give 2-anilino substituted pyridopyrimidines of the formulae (IV), (Ia, scheme 2) or (Ib). The reaction may be performed in excess aniline as the solvent or in an inert solvent like $CH_2Cl_2$, toluene, acetonitrile, DMF, dimethyl sulfoxide (DMSO) or NMP, and at temperatures in the range from 0° C. to 150° C. Acids like trifluoroacetic acid (TFA) or hydrochloric acid (HCl) may be added to catalyze the reaction. If mCPBA has been used for the previous oxidation step, the formed m-chlorobenzoic acid present in the crude reaction mixture may serve as the catalyst.

Steps 4 and 5:

The appropriate carboxylic acids of formulae (IV) or (II, scheme 2) can be converted into amide derivatives of the formulae (Ia, scheme 1) or (V) by standard procedures known in the art. For instance, the acid is first activated by reaction with a carbodiimide or carbonyl diimidazole or oxalyl chloride, and subsequently reacted without isolation with the appropriate substituted amine or ammonia. This reaction is best performed in an inert solvent like THF, $CH_2Cl_2$ or NMP at temperatures ranging from 0° C. to 150° C.

Step 8:

A suitable leaving group "L" in (VIII) may be a triflat, which can be prepared from (VII) by reaction with $Tf_2O$ or $PhN(Tf)_2$ in an inert solvent like THF or $CH_2Cl_2$ or NMP, in the presence of a base like $NEt_3$, pyridine, KOtBu, LDA, NaH, or $K_2CO_3$. Another leaving group is a chlorine or bromine atom which can be introduced by halogenation of the pyridone with $POCl_3$ or $POBr_3$.

Step 9:

The leaving group "L" in (VIII) can be substituted by an inorganic cyanide like potassium cyanide (KCN), sodium cyanide (NaCN) or copper cyanide (CuCN) in an inert solvent like diglyme, DMF, NMP, or sulfolane at temperatures from RT to 180° C., to give (IX). Preferably, this reaction can also be catalyzed by a transition metal catalyst, e.g. a Pd— or Ni catalyst. In this case, also zinc cyanide ($Zn(CN)_2$) may be applied as the cyanide source.

Certain side chains in $R^3$ or $R^2$ may require protection during the reaction sequences. Here standard protection and deprotection procedures being well known in the art may be applied. For instance, primary and secondary amines can be applied in t-butoxycarbonyl (Boc) or benzyloxycarbonyl protected form and the protecting group can be removed as a last reaction step by treatment with an acid like HCl or TFA.

The compounds of the general formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Ansel, H., et. al., Pharmaceutical Dosage Forms and Drug Delivery Systems, 6th ed., 1995, pp. 196 and 1456–1457.

The compounds according to this invention and their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A preferred pharmaceutical preparation was obtained by using the following procedure:
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenize.

The above described preparation yields micro-suspensions of the compounds of formula I with particle sizes between 1 and 10 μm. The suspensions are suitable for oral applications.

The activity of the compounds according to this invention as inhibitors for the src-family tyrosine kinases was shown by using the following assay.

SRC-Inhibitor-Assay Parameters:
Reaction mixture:
ATP 5 μM
Peptide (R+Ja133-Ro): 10 μM
  Ja133-Ro 196 nM
  Ro 9.8 μM
PT66 230 ng/ml
Assay buffer: 4 mM MgCl2
  2 mM TCEP
  50 mM HEPES
  0,1% Tween 20
  pH 7.3

Enzyme: 2.5 U/ml
Inhibitor: max. 25 μM
min. 0.42 nM

Material:
Eu-labelled phosphotyrosine antibody: -for Lck Cisbio Mab PT66-K,
  for Src EG&G Wallac PT66 Eu-W1024 (all commercially available).
Peptides: Ro: $NH_2$-A-E-E-E-I-Y-G-E-F-E-A-K-K-K-K-$CONH_2$ (SEQ ID NO: 1), and
  Ja133-Ro: Ja133-G-Aminocaprylic acid-A-E-E-E-I-Y-G-E-F-E-A-K-K-K-K-$CONH_2$ (SEQ ID NO: 2), wherein Ja133 is LightCycler-Red 640-N-hydroxy succinimide ester;
whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 μmol scale) of a Rink-Linker modified polystyrene solid phase by repeatedly conjugating an twenty fold excess of aminoacids each protected by temporary piperidine labile Fmoc- and permanent acid labile tert-Bu-, BOC- and Otert-Bu-groups depending on the side chain function. The substrate sequence AEEEIYGEFEAKKKK (SEQ ID NO: 1) was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased by Roche Diagnostics GmbH) and triethylamine. After 3 hrs. the resin was washed with Dimethylformamide and Isopropanol until the eluates of the blue resin got colo-rless. The fully protected and labeled peptide was removed from the solid phase and released from the permanent protecting groups by treatment with a mixture of 80% trifluoracetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by MALDI mass spectroscopy [2720.0].
Enzymes: Upstate Lck ($p56^{lck}$, active), Upstate Src ($p60^{c-src}$, partially purified) were purchased from UBI.
Time-resolved Fluorescence Assay: Reader: Perkin Elmer, Wallac Viktor 1420-040 multilabel counter; Liquid handling system: Beckman Coulter, Biomek 2000.

ATP, Tween 20, HEPES were purchased from Roche Molecular Biochemicals, $MgCl_2$ and $MnCl_2$ were purchased from Merck Eurolab, TCEP was purchased from Pierce, 384 Well low volume fluorescence plates was purchased from Falcon.

Assay Description:
At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (Excelfit).

| Ex-No. | Compound-Name | IC$_{50}$ src [μM] | IC$_{50}$ lck [μM] |
|---|---|---|---|
| 1 | 6-(2-Bromo-phenyl)-2-(4-morpholin-4-yl-phenylamino)-pyrido[2,3-d]pyrimidine-7-carboxylic acid piperidin-4-ylamide | 0.0107 | 0.0601 |
| 2 | 6-(2-Bromo-phenyl)-2-(3-methanesulfonyl-phenylamino)-pyrido[2,3-d]pyrimidine-7-carbonitrile | 0.033 | 0.1589 |
| 3-1 | 6-(2-Bromo-phenyl)-2-(4-morpholin-4-yl-phenylamino)-pyrido[2,3-d]pyrimidine-7-carboxylic acid amide | 0.003 | 0.023 |
| 3-2 | 6-(2-Bromo-phenyl)-2-[4-(2-diethylamino-ethoxy)-phenylamino]-pyrido[2,3-d]pyrimidine-7-carboxylic acid amide | 0.0044 | 0.0125 |
| 3-3 | 6-(2-Bromo-phenyl)-2-(3-methylsulfanyl-phenylamino)-pyrido[2,3-d]pyrimidine-7-carboxylic acid amide | 0.0078 | |
| 3-4 | 6-(2-Bromo-phenyl)-2-(4-sulfamoyl-phenylamino)-pyrido[2,3-d]pyrimidine-7-carboxylic acid amide | 0.0069 | 0.0738 |
| 3-5 | 6-(2-Bromo-phenyl)-2-(3-methylsulfamoylmethyl-phenylamino)-pyrido[2,3-d]pyrimidine-7-carboxylic acid amide | 0.0357 | 0.1101 |
| 3-6 | 6-(2-Bromo-phenyl)-2-[3-(2-hydroxy-ethanesulfonyl)-phenylamino]-pyrido[2,3-d]pyrimidine-7-carboxylic acid amide | 0.0225 | 0.1453 |
| 3-7 | 6-(2-Bromo-phenyl)-2-(3-methanesulfonyl-phenylamino)-pyrido[2,3-d]pyrimidine-7-carboxylic acid amide | 0.0166 | 0.1126 |
| 3-8 | 6-(2-Bromo-phenyl)-2-(3-methylsulfanyl-phenylamino)-pyrido[2,3-d]pyrimidine-7-carboxylic acid (2-dimethylamino-ethyl)-amide | 0.0017 | 0.0323 |
| 3-9 | 6-(2-Bromo-phenyl)-2-(4-morpholin-4-yl-phenylamino)-pyrido[2,3-d]pyrimidine-7-carboxylic acid (2-dimethylamino-ethyl)-amide | 0.0009 | 0.0121 |
| 3-10 | 6-(2-Bromo-phenyl)-2-[4-(2-diethylamino-ethoxy)-phenylamino]-pyrido[2,3-d]pyrimidine-7-carboxylic acid (2-dimethylamino-ethyl)-amide | 0.0016 | 0.0037 |
| 3-11 | 6-(2-Bromo-phenyl)-2-(4-fluoro-phenylamino)-pyrido[2,3-d]pyrimidine-7-carboxylic acid piperidin-4-ylamide | 0.0661 | 0.7742 |
| 3-12 | 6-(2-Bromo-phenyl)-2-(4-fluoro-phenylamino)-pyrido[2,3-d]pyrimidine-7-carboxylic acid (2-dimethylamino-ethyl)-amide | 0.0341 | 0.3497 |
| 3-13 | 6-(2-Bromo-phenyl)-2-(4-fluoro-phenylamino)-pyrido[2,3-d]pyrimidine-7-carboxylic acid (2-methoxy-ethyl)-amide | 0.1141 | 0.3603 |
| 3-14 | 6-(2-Bromo-phenyl)-2-(4-fluoro-phenylamino)-pyrido[2,3-d]pyrimidine-7-carboxylic acid (3-dimethylamino-propyl)-amide | 0.0217 | 0.233 |
| 3-15 | 6-(2-Bromo-phenyl)-2-(4-fluoro-phenylamino)-pyrido[2,3-d]pyrimidine-7-carboxylic acid (3-dimethylamino-2,2-dimethyl-propyl)-amide | 0.0415 | 0.2177 |
| 3-16 | 6-(2-Bromo-phenyl)-2-(4-fluoro-phenylamino)-pyrido[2,3-d]pyrimidine-7-carboxylic acid (2-acetylamino-ethyl)-amide | 0.0814 | 0.1893 |
| 3-17 | 6-(2-Bromo-phenyl)-2-(4-fluoro-phenylamino)-pyrido[2,3-d]pyrimidine-7-carboxylic acid (2-methylamino-ethyl)-amide | 0.0062 | 0.0398 |
| 3-18 | 1-[6-(2-Bromo-phenyl)-2-(4-fluoro-phenylamino)-pyrido[2,3-d]pyrimidine-7-carbonyl]semicarbazide | 0.0248 | 0.0684 |
| 3-19 | 6-(2-Bromo-phenyl)-2-(4-fluoro-phenylamino)-pyrido[2,3-d]pyrimidine-7-carboxylic acid (2-dimethylamino-ethyl)-methyl-amide | 0.2003 | 0.3572 |
| 3-20 | 6-(2-Bromo-phenyl)-2-(4-fluoro-phenylamino)-pyrido[2,3-d]pyrimidine-7-carboxylic acid carbamoylmethyl-amide | 0.0624 | 0.289 |
| 3-21 | 6-(2-Bromo-phenyl)-2-(4-fluoro-phenylamino)-pyrido[2,3-d]pyrimidine-7-carboxylic acid (1-methyl-piperidin-4-yl)-amide | 0.0962 | 0.6377 |
| 3-22 | 6-(2-Bromo-phenyl)-2-(4-fluoro-phenylamino)-pyrido[2,3-d]pyrimidine-7-carboxylic acid (2-morpholin-4-yl-ethyl)-amide | 0.158 | 0.6618 |
| 3-23 | 6-(2-Bromo-phenyl)-2-(4-fluoro-phenylamino)-pyrido[2,3-d]pyrimidine-7-carboxylic acid (2-dimethylamino-1-methyl-ethyl)-amide | 0.1949 | 0.5727 |
| 3-24 | 6-(2-Bromo-phenyl)-2-(4-fluoro-phenylamino)-pyrido[2,3-d]pyrimidine-7-carboxylic acid methylcarbamoylmethyl-amide | 0.1305 | 0.2055 |

-continued

| Ex-No. | Compound-Name | IC$_{50}$ src [µM] | IC$_{50}$ lck [µM] |
|---|---|---|---|
| 3-25 | 6-(2-Bromo-phenyl)-2-(4-fluoro-phenylamino)-pyrido[2,3-d]pyrimidine-7-carboxylic acid [2-(2-oxo-imidazolidin-1-yl)-ethyl]-amide | 0.1572 | 0.3703 |
| 3-26 | 6-(2-Bromo-phenyl)-2-(4-fluoro-phenylamino)-pyrido[2,3-d]pyrimidine-7-carboxylic acid [3-(2-oxo-pyrrolidin-1-yl)-propyl]-amide | 0.197 | 0.2751 |
| 3-27 | 6-(2-Bromo-phenyl)-2-(4-fluoro-phenylamino)-pyrido[2,3-d]pyrimidine-7-carboxylic acid (2-dimethylamino-propyl)-amide | 0.0239 | 0.1288 |
| 3-28 | (S)-6-(2-Bromo-phenyl)-2-(4-fluoro-phenylamino)-pyrido[2,3-d]pyrimidine-7-carboxylic acid pyrrolidin-3-ylamide | 0.0193 | 0.0627 |
| 3-29 | (R)-6-(2-Bromo-phenyl)-2-(4-fluoro-phenylamino)-pyrido[2,3-d]pyrimidine-7-carboxylic acid pyrrolidin-3-ylamide | 0.103 | 0.4293 |
| 3-30 | 6-(2-Bromo-phenyl)-2-(4-fluoro-phenylamino)-pyrido[2,3-d]pyrimidine-7-carboxylic acid dimethylcarbamoylmethyl-amide | 0.2467 | 0.1506 |
| 3-31 | 6-(2-Bromo-phenyl)-2-(4-fluoro-phenylamino)-pyrido[2,3-d]pyrimidine-7-carboxylic acid (3-methylamino-propyl)-amide | 0.0428 | 0.1003 |
| 3-32 | 6-(2-Bromo-phenyl)-2-(4-fluoro-phenylamino)-pyrido[2,3-d]pyrimidine-7-carboxylic acid (3-morpholin-4-yl-propyl)-amide | 0.1168 | 0.1955 |
| 3-33 | 6-(2-Bromo-phenyl)-2-(4-fluoro-phenylamino)-pyrido[2,3-d]pyrimidine-7-carboxylic acid [2-(1-methyl-pyrrolidin-2-yl)-ethyl]-amide | 0.0447 | 0.0969 |
| 3-34 | (R)-6-(2-Bromo-phenyl)-2-(4-fluoro-phenylamino)-pyrido[2,3-d]pyrimidine-7-carboxylic acid piperidin-3-ylamide | 0.0979 | 0.1269 |
| 3-35 | 6-(2-Bromo-phenyl)-2-(4-fluoro-phenylamino)-pyrido[2,3-d]pyrimidine-7-carboxylic acid (1-aza-bicyclo[2.2.2]oct-3-yl)-amide | 0.0731 | 0.2507 |
| 3-36 | 6-(2-Bromo-phenyl)-2-(4-fluoro-phenylamino)-pyrido[2,3-d]pyrimidine-7-carboxylic acid [2-(pyridin-2-ylamino)-ethyl]-amide | 0.1650 | 0.2555 |
| 3-37 | 6-(2-Bromo-phenyl)-2-(4-fluoro-phenylamino)-pyrido[2,3-d]pyrimidine-7-carboxylic acid (2-sulfamoyl-ethyl)-amide | 0.0210 | 0.1889 |
| 3-38 | 6-(2-Bromo-phenyl)-2-(4-fluoro-phenylamino)-pyrido[2,3-d]pyrimidine-7-carboxylic acid (3-hydroxy-propyl)-amide | 0.0918 | 0.4561 |
| 3-39 | 6-(2-Bromo-phenyl)-2-(4-fluoro-phenylamino)-pyrido[2,3-d]pyrimidine-7-carboxylic acid [2-(3H-imidazol-4-yl)-ethyl]-amide | 0.0243 | 0.1137 |
| 3-40 | 6-(2-Bromo-phenyl)-2-(4-fluoro-phenylamino)-pyrido[2,3-d]pyrimidine-7-carboxylic acid (2-methanesulfinyl-ethyl)-amide | 0.1486 | 0.5836 |
| 3-41 | 6-(2-Bromo-phenyl)-2-(4-fluoro-phenylamino)-pyrido[2,3-d]pyrimidine-7-carboxylic acid (1,5-dimethyl-1H-pyrazol-3-ylmethyl)-amide | 0.0260 | 0.1260 |
| 3-42 | 6-(2-Bromo-phenyl)-2-(4-fluoro-phenylamino)-pyrido[2,3-d]pyrimidine-7-carboxylic acid (4-carbamoyl-1H-pyrazol-3-yl)-amide | 0.0563 | 0.6938 |
| 3-43 | 6-(2-Bromo-phenyl)-2-(4-fluoro-phenylamino)-pyrido[2,3-d]pyrimidine-7-carboxylic acid [2-(2-hydroxy-ethanesulfinyl)-ethyl]-amide | 0.1289 | 0.8090 |
| 3-44 | 6-(2-Bromo-phenyl)-2-(4-morpholin-4-yl-phenylamino)-pyrido[2,3-d]pyrimidine-7-carboxylic acid (2-methylamino-ethyl)-amide | 0.001 | 0.0025 |
| 3-45 | 6-(2-Bromo-phenyl)-2-(4-fluoro-phenylamino)-pyrido[2,3-d]pyrimidine-7-carboxylic acid (2-hydroxy-ethyl)-amide | 0.0215 | 0.1554 |
| 3-46 | 6-(2-Bromo-phenyl)-2-(4-fluoro-phenylamino)-pyrido[2,3-d]pyrimidine-7-carboxylic acid N'-(2-dimethylamino-acetyl)-hydrazide | 0.0168 | 0.0381 |
| 3-47 | (S)-6-(2-Bromo-phenyl)-2-(4-fluoro-phenylamino)-pyrido[2,3-d]pyrimidine-7-carboxylic acid piperidin-3-ylamide | 0.0066 | 0.0275 |
| 3-48 | (R)-6-(2-Bromo-phenyl)-2-(4-fluoro-phenylamino)-pyrido[2,3-d]pyrimidine-7-carboxylic acid (pyrrolidin-2-ylmethyl)-amide | 0.0021 | 0.0381 |
| 3-49 | 6-(2-Bromo-phenyl)-2-(4-fluoro-phenylamino)-pyrido[2,3-d]pyrimidine-7-carboxylic acid (1H-pyrazol-3-yl)-amide | 0.0043 | 0.0073 |

-continued

| Ex-No. | Compound-Name | IC$_{50}$ src [µM] | IC$_{50}$ lck [µM] |
|---|---|---|---|
| 4-1 | 6-(2-Bromo-phenyl)-2-(4-morpholin-4-yl-phenylamino)-pyrido[2,3-d]pyrimidine-7-carbonitrile; compound with trifluoro-acetic acid | 0.0065 | 0.0201 |
| 4-2 | 6-(2-Bromo-phenyl)-2-[4-(2-diethylamino-ethoxy)-phenylamino]-pyrido[2,3-d]pyrimidine-7-carbonitrile | 0.0018 | 0.0051 |
| 4-3 | 6-(2-Bromo-phenyl)-2-[4-(2-hydroxy-ethoxy)-phenylamino]-pyrido[2,3-d]pyrimidine-7-carbonitrile | 0.0045 | 0.0499 |
| 4-4 | 6-(2-Bromo-phenyl)-2-[4-(2-ethylamino-ethoxy)-phenylamino]-pyrido[2,3-d]pyrimidine-7-carbonitrile | 0.0011 | 0.0042 |
| 4-5 | 6-(2-Bromo-phenyl)-2-(3-methanesulfinyl-phenylamino)-pyrido[2,3-d]pyrimidine-7-carbonitrile | 0.0035 | 0.0521 |
| 4-6 | 6-(2-Bromo-phenyl)-2-[3-(2-hydroxy-ethanesulfonyl)-phenylamino]-pyrido[2,3-d]pyrimidine-7-carbonitrile | 0.0162 | 0.0997 |
| 7-15 | 6-(2-Bromo-phenyl)-2-(4-morpholin-4-yl-phenylamino)-pyrido[2,3-d]pyrimidine-7-carboxylic acid (2-methanesulfonylamino-ethyl)-amide | 0.0004 | 0.0114 |
| 7-17 | 6-(2-Bromo-phenyl)-2-(3-methanesulfonylamino-phenylamino)-pyrido[2,3-d]pyrimidine-7-carboxylic acid (2-methanesulfonylamino-ethyl)-amide | 0.0035 | 0.0118 |
| 7-18 | 6-(2-Bromo-phenyl)-2-[4-(2-hydroxy-ethoxy)-phenylamino]-pyrido[2,3-d]pyrimidine-7-carboxylic acid (2-methanesulfonylamino-ethyl)-amide | 0.0088 | 0.0188 |
| 7-19 | 6-(2-Bromo-phenyl)-2-[4-(4-methyl-piperazin-1-yl)-phenylamino]-pyrido[2,3-d]pyrimidine-7-carboxylic acid (2-methanesulfonylamino-ethyl)-amide | 0.0010 | 0.0021 |
| 7-20 | 6-(2-Bromo-phenyl)-2-(3-methoxy-phenylamino)-pyrido[2,3-d]pyrimidine-7-carboxylic acid (2-methanesulfonylamino-ethyl)-amide | 0.0061 | 0.0111 |
| 7-21 | 2-(3-Acetylamino-phenylamino)-6-(2-bromo-phenyl)-pyrido[2,3-d]pyrimidine-7-carboxylic acid (2-methanesulfonylamino-ethyl)-amide | 0.0018 | 0.0120 |
| 7-22 | 6-(2-Bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (2-methanesulfonylamino-ethyl)-amide | 0.0050 | 0.0370 |
| 7-23 | 6-(2-Bromo-phenyl)-2-[3-(2-hydroxy-ethylsulfanyl)-phenylamino]-pyrido[2,3-d]pyrimidine-7-carboxylic acid (2-methanesulfonylamino-ethyl)-amide | 0.0010 | 0.0061 |
| 7-24 | 6-(2-Bromo-phenyl)-2-(3-hydroxymethyl-2,3-dihydro-benzo[1,4]dioxin-6-ylamino)-pyrido[2,3-d]pyrimidine-7-carboxylic acid (2-methanesulfonylamino-ethyl)-amide | 0.0040 | 0.0090 |
| 7-13 | 6-(2-Bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (2-sulfamoyl-ethyl)-amide | 0.0113 | 0.2320 |
| 7-4 | 6-(2-Bromo-phenyl)-2-(3-hydroxymethyl-phenylamino)-pyrido[2,3-d]pyrimidine-7-carboxylic acid (2-hydroxy-ethyl)-amide | 0.0309 | 0.0991 |

In Vivo Assay on Tumor Inhibition:

To generate primary tumors, HT-29 colon carcinoma cells ($2.5 \times 10^6$ in a volume of 100 µl) are injected subcutaneously into the left flank of female SCID mice using a 1 ml syringe and a 26G needle. The HT-29 cells are originally obtained from the NCI and deposited in a working cell bank. The cells are thawed and expanded in vitro before use in the experiment. Mice are assigned to the treatment groups on day 9. For grouping (n=12 mice per group), the animals are randomized to get a similar mean primary tumor volume of ca. 120 mm$^3$ per group. The test compounds are administered orally once per day as a suspension in 7.5% gelatine 0.22% NaCl with an administration volume of 10 ml/kg based on actual body weights. Treatment is initiated on day 10, and carried out until day 30, the final day of the study. The subcutaneous primary tumors are measured twice weekly, starting on day 7 after tumor cell implantation, in two dimensions (length and width) using an electronic caliper. The volume of the primary tumor is calculated using the formula: V[mm$^3$]=(length [mm]×width [mm]×width [mm])/2. In addition, the body weight of all animals is recorded at least twice weekly. Finally, at the end of the study the tumors are explanted and weighed.

Based on the above described pharmaceutically preparations and biological data, the present invention provides as further preferred embodiments a medicament containing one or more compounds of formula I as active ingredients together with pharmaceutically acceptable adjuvants;

a medicament as defined above for the treatment of diseases mediated by an inappropriate activation of src family tyrosine kinases;

a medicament as defined above for the treatment of cancer;

the use of one or more compounds of formula I as src family tyrosine kinase inhibitors;

the use of one or more compounds of formula I as cell signaling-regulating- and anti-proliferating agents;

the use of one or more compounds of formula I for the treatment of cancer;

the use of one ore more compounds of formula I for the production of medicaments for the treatment of diseases mediated by an inappropriate activation of src family tyrosine kinases;

the use of one ore more compounds of formula I for the production of medicaments for the inhibition of tumor growth; and the use of one ore more compounds of formula I for the production of medicaments for the treatment of cancer.

The following examples, references are provided to aid the understanding of the present invention, the true scope of which is set forth in the appended claims. It is understood that modifications can be made in the procedures set forth without departing from the spirit of the invention.

1) Starting Materials

EXAMPLE a 6-(2-Bromo-phenyl)-2-methylsulfanyl-pyrido[2,3-d] pyrimidine-7-carboxylic acid 3.372 g 3-(2-bromophenyl)2-oxopropionic acid in 20 ml DMF were treated with 4.434 g DBU under cooling and stirred for 10 min at RT. 2.728 g 4-amino-2-methylsulfanylpyrimidine-5-carbaldehyde were added and the mixture was stirred at 85° C. for 4.5 hrs. Stirring was continued over night at RT, then the solvent was evaporated and the residue dispensed in aqueous sodium carbonate solution. The mixture is extracted with ethyl acetate, then acidified to pH 2 and again extracted with chloroform. The chloroform extracts were dried and evaporated and the residue triturated with hot ethyl acetate. 2.786 g of the title product were thus obtained after filtration.

EXAMPLE b 6-(2-Bromo-phenyl)-2-methylsulfinyl-pyrido[2,3-d] pyrimidine-7-carboxylic acid 1 g of 70% mCPBA were dissolved in 20 ml methylene chloride and dried by filtration over sodium sulfate. This solution was added dropwise to a solution of 1 g of the compound from ex. a in 50 ml methylene chloride at RT. Stirring was continued for 2 hrs and the resulting mixture used directly for the next step.

EXAMPLE c 6-(2-Bromo-phenyl)-2-(4-fluoro-phenylamino)-pyrido[2,3-d]pyrimidine-7-carboxylic acid The crude solution from ex. b was treated directly with 0.325 g p-F-aniline and heated to reflux for 5 hrs. The solvent was evaporated and the residue purified by chromatography on silica, CH$_2$Cl$_2$/MeOH eluent. Product containing fractions were concentrated and the residue triturated with a small amount of methanol.

Yield 0.712 g of the title product.

EXAMPLE d

Trifluoromethanesulfonic acid 6-(2-bromo-phenyl)-2-methylsulfanyl-pyrido[2,3-d]pyrimidin-7-yl ester To a suspension of 0.43 mg 55% sodium hydride in 15 ml NMP were added 3.0 g of 6-(2-Bromo-phenyl)-2-methylsulfanyl-8H-pyrido[2,3-d]pyrimidin-7-one in portions at RT. Stirring was continued at 40° C. for 30 min, then the solution was cooled to RT and 5.85 g of N-phenyl-bis(trifluoromethanesulfonimide) were added. After 30 min stirring at RT, the solvent was evaporated and the residue purified by flash chromatography (silica, ethylacetate/hexanes) to give 3.85 g of the title product.

EXAMPLE e 6-(2-Bromo-phenyl)-2-methylsulfanyl-pyrido[2,3-d] pyrimidine-7-carbonitrile 1.95 g triflate from ex. d, 1.31 g tetrakis-(triphenylphosphino) palldium (0) and 0.381 g zinc cyanide were mixed in 20 ml NMP and stirred at 80° C. for 1 hr. Another 0.2 g catalyst were added and stirring continued for 2 hr 45. The NMP was removed by vacuum distillation and the residue chromatographed on silica (ethyl acetate/hexanes).

Yield 0.60 g of the title product.

EXAMPLE f 6-(2-Bromo-phenyl)-2-methylsulfanyl-pyrido[2,3-d] pyrimidine-7-carboxamide 0.509 g carboxylic acid from ex. a and 0.15 g triethyl amine were dissolved in 10 ml THF. At −50 C, 1.0 ml ethyl chloroformate (10 equivalents) were added and the mixture stirred for 30 min. 1.50 ml conc. aqueous ammonia were added and the mixture allowed to warm up to room temperature. The mixture was worked up with ethyl acetate and water, the water phases were extracted with chloroform and the organic phases concentrated and purified by chromatography on silica (ethyl acetate/hexanes). Yield 0.28 g of the title product.

EXAMPLE g 6-(2-Bromo-phenyl)-2-methylsulfanyl-pyrido[2,3-d] pyrimidine-7-carboxylic acid (2-methanesulfonylamino-ethyl)-amide 188 mg of the product of example a were dissolved in 2 ml DMF. 97 mg carbonyl diimidazole were added and the mixture stirred at RT for 1 hr. 104 mg 2-methylsulfonylamino-ethylamine dissolved in 2 ml DMF were added dropwise and stirring was continued for 1 hr with TLC control. The solvent was evaporated under vacuum and the residue purified by chromatography on silica, yielding 208 mg of the title product.

EXAMPLE h 6-(2-Bromo-phenyl)-2-methylsulfanyl-pyrido[2,3-d] pyrimidine-7-carboxylic acid ((S)-1-N-Boc-pyrrolidin-2-ylmethyl)-amide Analogous to example g, 376 mg of the product of example a and 300 mg (S)-2-aminomethyl-1-N-Boc-pyrrolidine (purchased from AstaTech Inc.) were coupled to give 470 mg of the title product.

EXAMPLE i

6-Nitro-2,3-dihydro-benzo[1,4]oxathiine-4,4-dioxide 2.554 g 66% H2SO4 and 1.454 g 65% nitric acid were mixed at 0° C. 2.395 g 2,3-dihydro-benzo[1,4]oxathiine-4,4-dioxide were added in portions at 0° C. After stirring for 30 min. the mixture was diluted with water and the product isolated by filtration. Chromatography on silica yielded 1.6 g of the title compound and 0.37 g 0.58 g of the 8-nitro isomer.

EXAMPLE j

6-Amino-2,3-dihydro-benzo[1,4]oxathiine-4,4-dioxide 0.917 g 6-Nitro-2,3-dihydro-benzo[1,4]oxathiine-4,4-dioxide (from g)) were hydrogenated in a mixture of 20 ml THF and 20 ml MeOH with 0.90 g 5% Pd—C at atmospheric hydrogen pressure for 90 min. at room temperature. The catalyst was filtered off, the filtrate evaporated and the residue chromatographed on silica to yield 370 mg of the title compound.

EXAMPLE k

2-Hydroxymethyl-7-nitro-1,4-benzodioxane 17.6 g 4-nitrocatechol and 11.0 g potassium bicarbonate were stirred in 200 ml DMF at 10° C. 13.99 g epibromohydrin in 10 ml DMF were added dropwise and stirring was continued at 60° C. for another 17 hrs. DMF was evaporated and the residue diluted with 50 ml water and extracted with ethyl acetate. The combined organic phases were washed with caustic soda and water, dried and evaporated. The crude oily product was heated to 90° C. with 200 ml toluene and the supernatant decanted from insoluble parts. After cooling to RT the solution is again decanted from insoluble oils and left at RT for 3 d. A first crop of 0.75 g crystalline title product was obtained. The mother liquor was evaporated and the residue dissolved in 20 dichloromethane at RT. Seeding and chilling to 0° C. yielded another 2.78 g crystalline title product.

EXAMPLE l

2-Hydroxymethyl-7-amino-1,4-benzodioxane 4.2 g of the nitro compound from example k in 120 ml MeOH were hydrogenated at atmospheric pressure with 10% Pd—C at room temperature for 3 hrs. The mixture was filtered and the filtrate evaporated to yield 3.13 g of the title compound.

Final Products

EXAMPLE 1

6-(2-Bromo-phenyl)-2-(4-morpholin-4-yl-phenylamino)-pyrido[2,3-d]pyrimidine-7-carboxylic acid piperidin-4-ylamide 62 mg 6-(2-Bromo-phenyl)-2-(4-morpholin-4-yl-phenylamino)-pyrido[2,3-d]pyrimidine-7-carboxylic acid were dissolved in 2 ml DMF. At RT 27 mg 4-Amino-piperidine-1-carboxylic acid tert-butyl ester, 16 mg 1-hydroxybenzotriazole, and finally 26 mg 1-(3-diethylaminopropyl)-3-ethylcarbodiimide hydrochloride were added and the mixture heated to 50° C. After 5 hrs the solvent was evaporated and the residue worked up with water and chloroform. The chloroform extracts were purified by chromatography over silica.

44 mg of this product were deprotected by stirring in 2 ml ethanol with 0.4 ml of a 2 M solution of HCl in ether. After 1 night at RT the mixture was evaporated and diluted with aqueous sodium carbonate solution. Extraction with ethyl acetate and further purification by chromatography (silica, $CHCl_3$/MeOH/$NH_3$ eluent) yielded 15 mg of the title product as a slightly yellow powder.

1H-NMR ($CDCl_3$, ppm): 1.45 (m, 2H), 1.93 (m, 2H), 2.63 (m, 2H), 3.03 (broad d, 2H), 3.10 (t, 4H), 3.82 (t, 4H), 3.87 (m, 1H), 6.92 (d, 2H), 7.26 (m, overlap with $CHCl_3$), 7.28 (m, 1H), 7.34 (m, 1H), 7.46 (s, 1H), 7.55 (d, 1H), 7.57 (broad signal, 2H), 7.88 (s, 1H), 7.93 (broad d, 1H), 9.07 (s, 1H).

EXAMPLE 2

6-(2-Bromo-phenyl)-2-(3-methanesulfonyl-phenylamino)-pyrido[2,3-d]pyrimidine-7-carbonitrile 60 mg of the starting material from ex. e in 3 ml chloroform were treated with 0.22 g 2-benzenesulfonyl-3-phenyl-oxaziridine at RT for 5 hrs. Excess oxidizing reagent was destroyed by addition of 52 mg dimethylsulfide and stirring for additional 75 min. Finally 0.244 g 3-methylsulfonylaniline hydrochloride were added and the mixture was stirred for 1 day at RT. 5 ml NMP were added and stirring continued for one more day. The mixture was diluted with water, the organic phase separated and washed with water. The organic phase was concentrated and the residue stirred with a mixture of 10 ml methanol and 5 water. Filtration yielded 42 mg of the title product as a pale yellow powder.

1H-NMR (DMSO-d6, ppm): 3.20 (s, 3H), 7.49 (m, 1H), 7.55–7.70 (m, 4H), 7.84 (d, 1H), 8.35 (broad d, 1H), 8.55 (broad s, 1H), 8.63 (s, 1H), 9.57 (s, 1H), 10.92 (s, 1H).

EXAMPLE 3

According to the synthesis procedure described in Example 1 and using the corresponding starting materials, the following compounds can be obtained:

3-1 6-(2-Bromo-phenyl)-2-(4-morpholin-4-yl-phenylamino)-pyrido[2,3-d]pyrimidine-7-carboxylic acid amide 3-2 6-(2-Bromo-phenyl)-2-[4-(2-diethylamino-ethoxy)-phenylamino]-pyrido[2,3-d]pyrimidine-7-carboxylic acid amide 3-3 6-(2-Bromo-phenyl)-2-(3-methylsulfanyl-phenylamino)-pyrido[2,3-d]pyrimidine-7-carboxylic acid amide 3-4 6-(2-Bromo-phenyl)-2-(4-sulfamoyl-phenylamino)-pyrido[2,3-d]pyrimidine-7-carboxylic acid amide 3-5 6-(2-Bromo-phenyl)-2-(3-methylsulfamoylmethyl-phenylamino)-pyrido[2,3-d]pyrimidine-7-carboxylic acid amide 3-6 6-(2-Bromo-phenyl)-2-[3-(2-hydroxy-ethanesulfonyl)-phenylamino]-pyrido[2,3-d]pyrimidine-7-carboxylic acid amide 3-7 6-(2-Bromo-phenyl)-2-(3-methanesulfonyl-phenylamino)-pyrido[2,3-d]pyrimidine-7-carboxylic acid amide 3-8 6-(2-Bromo-phenyl)-2-(3-methylsulfanyl-phenylamino)-pyrido[2,3-d]pyrimidine-7-carboxylic acid (2-dimethylamino-ethyl)-amide 3-9 6-(2-Bromo-phenyl)-2-(4-morpholin-4-yl-phenylamino)-pyrido[2,3-d]pyrimidine-7-carboxylic acid (2-dimethylamino-ethyl)-amide 3-10 6-(2-Bromo-phenyl)-2-[4-(2-diethylamino-ethoxy)-phenylamino]-pyrido[2,3-d]pyrimidine-7-carboxylic acid (2-dimethylamino-ethyl)-amide 3-11 6-(2-Bromo-phenyl)-2-(4-fluoro-phenylamino)-pyrido[2,3-d]pyrimidine-7-carboxylic acid piperidin-4-ylamide 3-12 6-(2-Bromo-phenyl)-2-(4-fluoro-phenylamino)-pyrido[2,3-d]pyrimidine-7-carboxylic acid (2-dimethylamino-ethyl)-amide 3-13 6-(2-Bromo-phenyl)-2-(4-fluoro-phenylamino)-pyrido[2,3-d]pyrimidine-7-carboxylic acid (2-methoxy-ethyl)-amide 3-14 6-(2-Bromo-phenyl)-2-(4-fluoro-phenylamino)-pyrido[2,3-d]pyrimidine-7-carboxylic acid (3-dimethylamino-propyl)-amide 3-15 6-(2-Bromo-phenyl)-2-(4-fluoro-phenylamino)-pyrido[2,3-d]pyrimidine-7-carboxylic acid (3-dimethylamino-2,2-dimethyl-propyl)-amide 3-16 6-(2-Bromo-phenyl)-2-(4-fluoro-phenylamino)-pyrido[2,3-d]pyrimidine-7-carboxylic acid (2-acetylamino-ethyl)-amide 3-17 6-(2-Bromo-phenyl)-2-(4-fluoro-phenylamino)-pyrido[2,3-d]pyrimidine-7-carboxylic acid (2-methylamino-ethyl)-amide 3-18 1-[6-(2-Bromo-phenyl)-2-(4-fluoro-phenylamino)-pyrido[2,3-d]pyrimidine-7-carbonyl]semicarbazide 3-19 6-(2-Bromo-phenyl)-2-(4-fluoro-phenylamino)-pyrido[2,3-d]pyrimidine-7-carboxylic acid (2-dimethylamino-ethyl)-methyl-amide 3-20 6-(2-Bromo-phenyl)-2-(4-fluoro-phenylamino)-pyrido[2,3-d]pyrimidine-7-carboxylic acid carbamoylmethyl-amide 3-21 6-(2-Bromo-phenyl)-2-(4-fluoro-phenylamino)-pyrido[2,3-d]pyrimidine-7-carboxylic acid (1-methyl-piperidin-4-yl)-amide 3-22 6-(2-Bromo-phenyl)-2-(4-fluoro-phenylamino)-pyrido[2,3-d]pyrimidine-7-carboxylic acid (2-morpholin-4-yl-ethyl)-amide 3-23 6-(2-Bromo-phenyl)-2-(4-fluoro-phenylamino)-pyrido[2,3-d]pyrimidine-7-carboxylic acid (2-dimethylamino-1-methyl-ethyl)-amide 3-24 6-(2-Bromo-phenyl)-2-(4-fluoro-phenylamino)-pyrido[2,3-d]pyrimidine-7-carboxylic acid methylcarbamoylmethyl-amide 3-25 6-(2-Bromo-phenyl)-2-(4-fluoro-phenylamino)-pyrido[2,3-d]pyrimidine-7-carboxylic acid[2-(2-oxo-imidazolidin-1-yl)-ethyl]-amide 3-26 6-(2-Bromo-phenyl)-2-(4-fluoro-phenylamino)-pyrido[2,3-d]pyrimidine-7-carboxylic acid [3-(2-oxo-pyrrolidin-1-yl)-propyl]-amide 3-27 6-(2-Bromo-phenyl)-2-(4-fluoro-phenylamino)-pyrido[2,3-d]pyrimidine-7-carboxylic acid (2-dimethylamino-propyl)-amide 3-28 (S)-6-(2-Bromo-phenyl)-2-(4-fluoro-phenylamino)-pyrido[2,3-d]pyrimidine-7-carboxylic acid pyrrolidin-3-ylamide 3-29 (R)-6-(2-Bromo-phenyl)-2-(4-fluoro-phenylamino)-pyrido[2,3-d]pyrimidine-7-carboxylic acid pyrrolidin-3-ylamide 3-30 6-(2-Bromo-phenyl)-2-(4-fluoro-phenylamino)-pyrido[2,3-d]pyrimidine-7-carboxylic acid dimethylcarbamoylmethyl-amide 3-31 6-(2-Bromo-phenyl)-2-(4-fluoro-phenylamino)-pyrido[2,3-d]pyrimidine-7-carboxylic acid (3-methylamino-propyl)-amide 3-32 6-(2-Bromo-phenyl)-2-(4-fluoro-phenylamino)-pyrido[2,3-d]pyrimidine-7-carboxylic acid (3-morpholin-4-yl-propyl)-amide 3-33 6-(2-Bromo-phenyl)-2-(4-fluoro-phenylamino)-pyrido[2,3-d]pyrimidine-7-carboxylic acid [2-(1-methyl-pyrrolidin-2-yl)-ethyl]-amide 3-34 (R)-6-(2-Bromo-phenyl)-2-(4-fluoro-phenylamino)-pyrido[2,3-d]pyrimidine-7-carboxylic acid piperidin-3-ylamide 3-35 6-(2-Bromo-phenyl)-2-(4-fluoro-phenylamino)-pyrido[2,3-d]pyrimidine-7-carboxylic acid (1-aza-bicyclo[2.2.2]oct-3-yl)-amide 3-36 6-(2-Bromo-phenyl)-2-(4-fluoro-phenylamino)-pyrido[2,3-d]pyrimidine-7-carboxylic acid [2-(pyridin-2-ylamino)-ethyl]-amide 3-37 6-(2-Bromo-phenyl)-2-(4-fluoro-phenylamino)-pyrido[2,3-d]pyrimidine-7-carboxylic acid (2-sulfamoyl-ethyl)-amide 3-38 6-(2-Bromo-phenyl)-2-(4-fluoro-phenylamino)-pyrido[2,3-d]pyrimidine-7-carboxylic acid (3-hydroxy-propyl)-amide 3-39 6-(2-Bromo-phenyl)-2-(4-fluoro-phenylamino)-pyrido[2,3-d]pyrimidine-7-carboxylic acid [2-(3H-imidazol-4-yl)-ethyl]-amide 3-40 6-(2-Bromo-phenyl)-2-(4-fluoro-phenylamino)-pyrido[2,3-d]pyrimidine-7-carboxylic acid (2-methanesulfinyl-ethyl)-amide 3-41 6-(2-Bromo-phenyl)-2-(4-fluoro-phenylamino)-pyrido[2,3-d]pyrimidine-7-carboxylic acid (1,5-dimethyl-1H-pyrazol-3-ylmethyl)-amide 3-42 6-(2-Bromo-phenyl)-2-(4-fluoro-phenylamino)-pyrido[2,3-d]pyrimidine-7-carboxylic acid (4-carbamoyl-1H-pyrazol-3-yl)-amide 3-43 6-(2-Bromo-phenyl)-2-(4-fluoro-phenylamino)-pyrido[2,3-d]pyrimidine-7-carboxylic acid [2-(2-hydroxy-ethanesulfinyl)-ethyl]-amide 3-44 6-(2-Bromo-phenyl)-2-(4-morpholin-4-yl-phenylamino)-pyrido[2,3-d]pyrimidine-7-carboxylic acid (2-methylamino-ethyl)-amide 3-45 6-(2-Bromo-phenyl)-2-(4-fluoro-phenylamino)-pyrido[2,3-d]pyrimidine-7-carboxylic acid (2-hydroxy-ethyl)-amide 3-46 6-(2-Bromo-phenyl)-2-(4-fluoro-phenylamino)-pyrido[2,3-d]pyrimidine-7-carboxylic acid N'-(2-dimethylamino-acetyl)-hydrazide 3-47 (S)-6-(2-Bromo-phenyl)-2-(4-fluoro-phenylamino)-pyrido[2,3-d]pyrimidine-7-carboxylic acid piperidin-3-ylamide 3-48 (R)-6-(2-Bromo-phenyl)-2-(4-fluoro-phenylamino)-pyrido[2,3-d]pyrimidine-7-carboxylic acid (pyrrolidin-2-ylmethyl)-amide 3-49 6-(2-Bromo-phenyl)-2-(4-fluoro-phenylamino)-pyrido[2,3-d]pyrimidine-7-carboxylic acid (1H-pyrazol-3-yl)-amide 3-50 6-(2-Bromo-phenyl)-2-(4-fluoro-phenylamino)-pyrido[2,3-d]pyrimidine-7-carboxylic acid (2-methyl-2H-pyrazol-3-yl)-amide 3-51 (S)-6-(2-Bromo-phenyl)-2-(4-fluoro-phenylamino)-pyrido[2,3-d]pyrimidine-7-carboxylic acid (2,3-dihydroxy-propyl)-amide 3-60 (R)-6-(2-Bromo-phenyl)-2-(4-fluoro-phenylamino)-pyrido[2,3-d]pyrimidine-7-carboxylic acid (2,3-dihydroxy-propyl)-amide 3-61 6-(2-Bromo-phenyl)-2-(4-fluoro-phenylamino)-pyrido[2,3-d]pyrimidine-7-carboxylic acid (piperidin-2-ylmethyl)-amide 3-62 6-(2-Bromo-phenyl)-2-(4-morpholin-4-yl-phenylamino)-pyrido[2,3-d]pyrimidine-7-carboxylic acid [2-(3H-imidazol-4-yl)-ethyl]-amide 3-63 6-(2-Bromo-phenyl)-2-(4-morpholin-4-yl-phenylamino)-pyrido[2,3-d]pyrimidine-7-carboxylic acid (S)-piperidin-3-ylamide 3-64 6-(2-Bromo-phenyl)-2-(4-fluoro-phenylamino)-pyrido[2,3-d]pyrimidine-7-carboxylic acid ((S)-pyrrolidin-2-ylmethyl)-amide

EXAMPLE 4

According to the synthesis procedure described in Example 2 and using the corresponding starting materials, the following compounds can be obtained:

4-1 6-(2-Bromo-phenyl)-2-(4-morpholin-4-yl-phenylamino)-pyrido[2,3-d]pyrimidine-7-carbonitrile; compound with trifluoro-acetic acid 4-2 6-(2-Bromo-phenyl)-2-[4-(2-diethylamino-ethoxy)-phenylamino]-pyrido[2,3-d]pyrimidine-7-carbonitrile 4-3 6-(2-Bromo-phenyl)-2-[4-(2-hydroxy-ethoxy)-phenylamino]-pyrido[2,3-d]pyrimidine-7-carbonitrile 4-4 6-(2-Bromo-phenyl)-2-[4-(2-ethylamino-ethoxy)-phenylamino]-pyrido[2,3-d]pyrimidine-7-carbonitrile 4-5 6-(2-Bromo-phenyl)-2-(3-methanesulfinyl-phenylamino)-pyrido[2,3-d]pyrimidine-7-carbonitrile 4-6 6-(2-Bromo-phenyl)-2-[3-(2-hydroxy-ethanesulfonyl)-phenylamino]-pyrido[2,3-d]pyrimidine-7-carbonitrile

EXAMPLE 5

6-(2-Bromo-phenyl)-2-[3-(2-hydroxyethylsulfanyl)-phenylamino]-pyrido[2,3-d]pyrimidine-7-carboxylic Acid (2-methanesulfonylamino-ethyl)-amide 2.6 g m-chloroperbenzoic acid (MCPBA, purchased from Aldrich, 57–86%) were dissolved in 20 ml dichloromethane and dried by filtration over sodium sulfate. 2 ml of this solution were added at 0–5° C. to a solution of 480 mg (0,97 mmol) of the product from example g in 3 ml dichloromethane. The mixture was allowed to reach RT and monitored by TLC. After 20 min another 0.1 ml of the above MCPBA solution were added at RT and stirring was continued for 10 min. Excess peracid was quenched by addition of 30 µl dimethylsulfide and stirring for another 20 min. The resulting mixture was used immediately without further purification for the next step: 0.625 ml of the above solution (containing 0.12 mmol) were added at RT to a solution of 22 mg meta-(2-hydroxyethylthio)aniline (0.13 mmol) in 0.5 ml dichloromethane. After 15 hrs the mixture was diluted with 10 ml dichloromethane and washed with aqueous acetic acid and with saturated potassium bicarbonate solution. Purification by chromatography on silica yielded 52 mg of the title product.

EXAMPLE 6

6-(2-Bromo-phenyl)-2-(3-methylsulfanyl-phenylamino)-pyrido[2,3-d]pyrimidine-7-carboxylic acid (pyrrolidin-2-ylmethyl)-amide Analogous to example 5, starting with 279 mg of the intermediate from example h, 250 mg of the title product was obtained in N-Boc protected form. The Boc protecting group was cleaved by stirring in dichloromethane with 2.5 ml of a 2M solution of HCl in ether at RT over night. The mixture was washed with aqueous sodium hydroxide and water and further purified by chromatography on silica ($CH_2Cl_2$/MeOH 95/5+1% $NH_4OH$). Yield 127 mg of the title product.

EXAMPLE 7

According to the synthesis procedure described in Example 5 and using the corresponding starting materials, the following compounds can be obtained:

7-1 6-(2-bromo-phenyl)-2-(4-morpholin-4-yl-phenylamino)-pyrido[2,3-d]pyrimidine-7-carboxylic acid (2-sulfamoyl-ethyl)-amide 7-2 6-(2-bromo-phenyl)-2-(3-methylsulfanyl-phenylamino)-pyrido[2,3-d]pyrimidine-7-carboxylic acid (2-sulfamoyl-ethyl)-amide 7-3 6-(2-bromo-phenyl)-2-(4-morpholin-4-yl-phenylamino)-pyrido[2,3-d]pyrimidine-7-carboxylic acid (2-hydroxy-ethyl)-amide 7-4 6-(2-bromo-phenyl)-2-(3-hydroxymethyl-phenylamino)-pyrido[2,3-d]pyrimidine-7-carboxylic acid (2-hydroxy-ethyl)-amide 7-5 6-(2-bromo-phenyl)-2-(4-methanesulfinyl-phenylamino)-pyrido[2,3-d]pyrimidine-7-carboxylic acid (2-hydroxy-ethyl)-amide 7-6 6-(2-bromo-phenyl)-2-(3-methanesulfinyl-phenylamino)-pyrido[2,3-d]pyrimidine-7-carboxylic acid (2-hydroxy-ethyl)-amide 7-7 6-(2-bromo-phenyl)-2-[3-(2-hydroxy-ethylsulfamoyl)-phenylamino]-pyrido[2,3-d]pyrimidine-7-carboxylic acid (2-hydroxy-ethyl)-amide 7-8 6-(2-bromo-phenyl)-2-[4-(2-hydroxy-ethylsulfamoyl)-phenylamino]-pyrido[2,3-d]pyrimidine-7-carboxylic acid (2-hydroxy-ethyl)-amide 7-9 6-(2-bromo-phenyl)-2-(3-hydroxymethyl-phenylamino)-pyrido[2,3-d]pyrimidine-7-carboxylic acid (2-sulfamoyl-ethyl)-amide 7-10 6-(2-bromo-phenyl)-2-(4-methanesulfinyl-phenylamino)-pyrido[2,3-d]pyrimidine-7-carboxylic acid (2-sulfamoyl-ethyl)-amide 7-11 6-(2-bromo-phenyl)-2-(3-methanesulfinyl-phenylamino)-pyrido[2,3-d]pyrimidine-7-carboxylic acid (2-sulfamoyl-ethyl)-amide 7-12 6-(2-bromo-phenyl)-2-[4-(2-hydroxy-ethoxy)-phenylamino]-pyrido[2,3-d]pyrimidine-7-carboxylic acid (2-sulfamoyl-ethyl)-amide 7-13 6-(2-bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (2-sulfamoyl-ethyl)-amide 7-14 6-(2-bromo-phenyl)-2-(3-methanesulfonyl-phenylamino)-pyrido[2,3-d]pyrimidine-7-carboxylic acid (2-sulfamoyl-ethyl)-amide 7-15 6-(2-bromo-phenyl)-2-(4-morpholin-4-yl-phenylamino)-pyrido[2,3-d]pyrimidine-7-carboxylic acid (2-methanesulfonylamino-ethyl)-amide 7-16 6-(2-bromo-phenyl)-2-(4-morpholin-4-yl-phenylamino)-pyrido[2,3-d]pyrimidine-7-carboxylic acid (2-[1,2,3]triazol-1-yl-ethyl)-amide 7-17 6-(2-bromo-phenyl)-2-(3-methanesulfonylamino-phenylamino)-pyrido[2,3-d]pyrimidine-7-carboxylic acid (2-methanesulfonylamino-ethyl)-amide 7-18 6-(2-bromo-phenyl)-2-[4-(2-hydroxy-ethoxy)-phenylamino]-pyrido[2,3-d]pyrimidine-7-carboxylic acid (2-methanesulfonylamino-ethyl)-amide 7-19 6-(2-bromo-phenyl)-2-[4-(4-methyl-piperazin-1-yl)-phenylamino]-pyrido[2,3-d]pyrimidine-7-carboxylic acid (2-methanesulfonylamino-ethyl)-amide 7-20 6-(2-bromo-phenyl)-2-(3-methoxy-phenylamino)-pyrido[2,3-d]pyrimidine-7-carboxylic acid (2-methanesulfonylamino-ethyl)-amide 7-21 2-(3-acetylamino-phenylamino)-6-(2-bromo-phenyl)-pyrido[2,3-d]pyrimidine-7-carboxylic acid (2-methanesulfonylamino-ethyl)-amide 7-22 6-(2-bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (2-methanesulfonylamino-ethyl)-amide 7-23 6-(2-bromo-phenyl)-2-[3-(2-hydroxy-ethylsulfanyl)-phenylamino]-pyrido[2,3-d]pyrimidine-7-carboxylic acid (2-methanesulfonylamino-ethyl)-amide 7-24 6-(2-bromo-phenyl)-2-(3-hydroxymethyl-2,3-dihydro-benzo[1,4]dioxin-6-ylamino)-pyrido[2,3-d]pyrimidine-7-carboxylic acid (2-methanesulfonylamino-ethyl)-amide

EXAMPLE 8

According to the synthesis procedure described in Example 6 and using the corresponding starting materials, the following compounds can be obtained:

8-1 6-(2-bromo-phenyl)-2-(3-methylsulfanyl-phenylamino)-pyrido[2,3-d]pyrimidine-7-carboxylic acid (s)-piperidin-3-ylamide 8-2 6-(2-bromo-phenyl)-2-(3-methylsulfanyl-phenylamino)-pyrido[2,3-d]pyrimidine-7-carboxylic acid (2-methylamino-ethyl)-amide 8-3 6-(2-bromo-phenyl)-2-(3-methylsulfanyl-phenylamino)-pyrido[2,3-d]pyrimidine-7-carboxylic acid ((s)-pyrrolidin-2-ylmethyl)-amide 8-4 6-(2-bromo-phenyl)-2-(4-morpholin-4-yl-phenylamino)-pyrido[2,3-d]pyrimidine-7-carboxylic acid ((s)-pyrrolidin-2-ylmethyl)-amide 8-5 6-(2-bromo-phenyl)-2-(4-morpholin-4-yl-phenylamino)-pyrido[2,3-d]pyrimidine-7-carboxylic acid ((r)-pyrrolidin-2-ylmethyl)-amide 8-6 6-(2-bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (pyrrolidin-2-ylmethyl)-amide HCl salt 8-7 6-(2-bromo-phenyl)-2-(3-methanesulfonylamino-phenylamino)-pyrido[2,3-d]pyrimidine-7-carboxylic acid (pyrrolidin-2-ylmethyl)-amide HCl salt 8-8 2-(3-acetylamino-phenylamino)-6-(2-bromo-phenyl)-pyrido[2,3-d]pyrimidine-7-carboxylic acid (pyrrolidin-2-ylmethyl)-amide HCl salt.

What is claimed is:

1. Compounds of formula I:

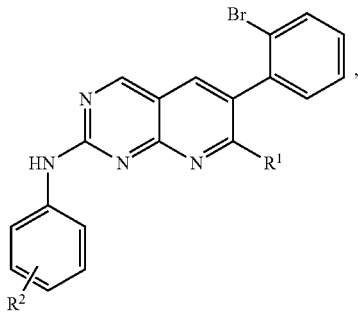

(formula I)

wherein
R[1] is —C(O)—NH-alkyl or —C(O)—N(alkyl)$_2$, which alkyl groups are unsubstituted or substituted with at least one substituent selected from the group consisting of:
—OH;
—NH(alkyl);
—N(alkyl)$_2$;
—NH—C(O)-alkyl;
—C(O)—NH-alkyl;
—C(O)—N(alkyl)$_2$;
—C(O)—NH$_2$;
—O-alkyl;
-heterocyclyl;
—NH-heterocyclyl;
—NH—S(O)$_2$-alkyl;
—S(O)$_2$—NH$_2$; and
—S(O)-alkyl,
wherein when said at least one substituent contains an alkyl group, the alkyl group is unsubstituted or substituted with —OH;
or a group
—CN;
—C(O)—NH$_2$;
—C(O)—NH-heterocyclyl;
—C(O)—NH—NH—C(O)—NH$_2$; or
—C(O)—NH—NH—C(O)-alkyl, which alkyl is unsubstituted or substituted with
—NH(alkyl); or
—N(alkyl)$_2$; and
R[2] is halogen;
heterocyclyl;
alkyl;
—NH—C(O)-alkyl;
—NH—S(O)$_2$-alkyl;
—(CH$_2$)$_m$—S(O)$_2$—NH$_2$;
—(CH$_2$)$_m$—S(O)$_2$—N(alkyl)$_2$;
—(CH$_2$)$_m$—S(O)$_2$—NH—(alkyl);
—O-alkyl; or
—S(O)$_n$-alkyl,
wherein when R[2] contains an alkyl group, the alkyl group is unsubstituted or substituted by
—OH;
—O-alkyl;
—NH-alkyl; or
—N(alkyl)$_2$;
m is 0, 1, 2, 3, 4, 5 or 6;
n is 0, 1 or 2;
or pharmaceutically acceptable salts thereof.

2. The compounds of formula I according to claim 1, wherein:
R[1] is —C(O)—NH-alkyl or —C(O)—N(alkyl)$_2$, which alkyl groups are unsubstituted or substituted with at least one substituent selected from the group consisting of:
—OH;
—NH(alkyl);
—N(alkyl)$_2$;
—NH—C(O)-alkyl;
—C(O)—NH-alkyl;
—C(O)—N(alkyl)$_2$;
—C(O)—NH$_2$;
—O-alkyl;
-heterocyclyl;
—NH-heterocyclyl;
—S(O)$_2$—NH$_2$; and
—S(O)-alkyl,
wherein when said at least one substituent contains an alkyl group, the alkyl group is unsubstituted or substituted with —OH;
or a group
—CN;
—C(O)—NH2;
—C(O)—NH-heterocyclyl;
—C(O)—NH—NH—C(O)—NH2; or
—C(O)—NH—NH—C(O)-alkyl, which alkyl is unsubstituted or substituted with
—NH(alkyl); or
—N(alkyl)$_2$; and
R[2] is halogen;
heterocyclyl;
—(CH$_2$)$_m$—S(O)$_2$—NH$_2$;
—(CH$_2$)$_m$—S(O)$_2$—N(alkyl)$_2$;
—(CH$_2$)$_m$—S(O)$_2$—NH—(alkyl);
—O-alkyl; or
—S(O)$_n$-alkyl, which alkyl groups are optionally substituted by
—OH;
—O—(C$_1$–C$_4$)alkyl;
—NH-alkyl; or
—N(alkyl)$_2$;
m is 0, 1, 2, 3, 4, 5 or 6;
n is 0, 1 or 2;
or pharmaceutically acceptable salts thereof.

3. The compounds according to claim 2,
wherein R[2] is halogen;
or pharmaceutically acceptable salts thereof.

4. The compounds according to claim 2, wherein:
R[2] is morpholin-4-yl;
—S-alkyl; or a group
—O-alkyl, which alkyl group is substituted with
—N(alkyl)$_2$;
or pharmaceutically acceptable salts thereof.

5. A compound according to claim 4, said compound selected from the group consisting of:
6-(2-Bromo-phenyl)-2-(3-methylsulfanyl-phenylamino)-pyrido[2,3-d]pyrimidine-7-carboxylic acid ((S)-pyrrolidin-2-ylmethyl)-amide,
6-(2-Bromo-phenyl)-2-(4-morpholin-4-yl-phenylamino)-pyrido[2,3-d]pyrimidine-7-carboxylic acid ((S)-pyrrolidin-2-ylmethyl)-amide,
6-(2-Bromo-phenyl)-2-(4-morpholin-4-yl-phenylamino)-pyrido[2,3-d]pyrimidine-7-carboxylic acid ((R)-pyrrolidin-2-ylmethyl)-amide, and 6-(2-Bromo-phenyl)-2-(4-morpholin-4-yl-phenylamino)-pyrido[2,3-d]pyrimidine-7-carboxylic acid (2-[1,2,3]triazol-1-yl-ethyl)-amide.

6. The compounds according to claim 2, wherein:
$R^1$ is —C(O)—NH-alkyl, which alkyl group is substituted with
 —OH;
 —NH(alkyl);
 —N(alkyl)$_2$; or
 —S(O)$_2$—NH$_2$;
or a group
 —C(O)—NH-piperidin-3-yl;
 —C(O)—NH-pyrrolidin-3-yl;
 —C(O)—NH—CH$_2$-pyrrolidin-2-yl; or
 —C(O)—NH—(CH$_2$)$_2$-imidazol-4-yl; and
$R^2$ is morpholin-4-yl;
 —S-alkyl;
 —O-alkyl, which alkyl group is substituted with
  —N(alkyl)$_2$; or
 —S(O)$_2$—NH-alkyl, which alkyl group is substituted with
  —OH; or
  —O—(C$_1$–C$_4$)alkyl;
or pharmaceutically acceptable salts thereof.

7. A compound according to claim 6, said compound selected from the group consisting of:
 6-(2-Bromo-phenyl)-2-(4-morpholin-4-yl-phenylamino)-pyrido[2,3-d]pyrimidine-7-carboxylic acid [2-(3H-imidazol-4-yl)-ethyl]-amide,
 6-(2-Bromo-phenyl)-2-(4-morpholin-4-yl-phenylamino)-pyrido[2,3-d]pyrimidine-7-carboxylic acid (S)-piperidin-3-ylamide,
 6-(2-Bromo-phenyl)-2-(3-methylsulfanyl-phenylamino)-pyrido[2,3-d]pyrimidine-7-carboxylic acid (S)-piperidin-3-ylamide,
 6-(2-Bromo-phenyl)-2-(4-morpholin-4-yl-phenylamino)-pyrido[2,3-d]pyrimidine-7-carboxylic acid (2-sulfamoyl-ethyl)-amide,
 6-(2-Bromo-phenyl)-2-(3-methylsulfanyl-phenylamino)-pyrido[2,3-d]pyrimidine-7-carboxylic acid (2-sulfamoyl-ethyl)-amide, and
 6-(2-Bromo-phenyl)-2-(4-morpholin-4-yl-phenylamino)-pyrido[2,3-d]pyrimidine-7-carboxylic acid (2-hydroxy-ethyl)-amide.

8. The compounds according to claim 2, wherein:
$R^1$ is —C(O)—NH-alkyl, which alkyl group is substituted with
 —OH;
 —NH(alkyl);
 —N(alkyl)$_2$; or
 —S(O)$_2$—NH$_2$; and
$R^2$ is morpholin-4-yl;
or pharmaceutically acceptable salts thereof.

9. The compounds according to claim 2, wherein:
$R^1$ is —C(O)—NH-alkyl, which alkyl group is substituted with
 —OH;
 —NH(alkyl);
 —N(alkyl)$_2$; or
 —S(O)$_2$—NH$_2$; and
$R^2$ is —S-alkyl;
or pharmaceutically acceptable salts thereof.

10. The compounds according to claim 2, wherein:
$R^1$ is —C(O)—NH-alkyl, which alkyl group is substituted with
 —OH;
 —NH(alkyl);
 —N(alkyl)$_2$; or
 —S(O)$_2$—NH$_2$; and
$R^2$ is —O-alkyl, which alkyl group is substituted with
 —N(alkyl)$_2$;
or pharmaceutically acceptable salts thereof.

11. The compounds according to claim 2, wherein:
$R^1$ is —C(O)—NH-alkyl, which alkyl group is substituted with
 —OH;
 —NH(alkyl);
 —N(alkyl)$_2$; or
 —S(O)$_2$—NH$_2$; and
$R^2$ is —S(O)$_2$—NH-alkyl, which alkyl group is substituted with
 —OH; or
 —O—(C$_1$–C$_4$)alkyl;
or pharmaceutically acceptable salts thereof.

12. The compounds according to claim 2, wherein:
$R^1$ is —C(O)—NH-piperidin-3-yl;
 —C(O)—NH-pyrrolidin-3-yl;
 —C(O)—NH—CH$_2$-pyrrolidin-2-yl; or
 —C(O)—NH—(CH$_2$)$_2$-imidazol-4-yl; and
$R^2$ is morpholin-4-yl;
or pharmaceutically acceptable salts thereof.

13. The compounds according to claim 2, wherein:
$R^1$ is —C(O)—NH-piperidin-3-yl;
 —C(O)—NH-pyrrolidin-3-yl;
 —C(O)—NH—CH$_2$-pyrrolidin-2-yl; or
 —C(O)—NH—(CH$_2$)$_2$-imidazol-4-yl; and
R2 is —S-alkyl;
or pharmaceutically acceptable salts thereof.

14. The compounds according to claim 2, wherein:
$R^1$ is —C(O)—NH-piperidin-3-yl;
 —C(O)—NH-pyrrolidin-3-yl;
 —C(O)—NH—CH$_2$-pyrrolidin-2-yl; or
 —C(O)—NH—(CH$_2$)$_2$-imidazol-4-yl; and
$R^2$ is —O-alkyl, which alkyl group is substituted with
 —N(alkyl)$_2$;
or pharmaceutically acceptable salts thereof.

15. The compounds according to claim 2, wherein:
$R^1$ is —C(O)—NH-piperidin-3-yl;
 —C(O)—NH-pyrrolidin-3-yl;
 —C(O)—NH—CH$_2$-pyrrolidin-2-yl; or
 —C(O)—NH—(CH$_2$)$_2$-imidazol-4-yl; and
$R^2$ is —S(O)$_2$—NH-alkyl, which alkyl group is substituted with
 —OH; or
 —O—(C$_1$–C$_4$)alkyl;
or pharmaceutically acceptable salts thereof.

16. The compounds according to claim 2, wherein:
$R^1$ is —CN;
$R^2$ is morpholin-4-yl;
 —S-alkyl;
 —O-alkyl, which alkyl group is substituted with
  —N(alkyl)$_2$; or
 —S(O)$_2$—NH-alkyl, which alkyl group is substituted with
  —OH; or
  —O—(C$_1$–C$_4$)alkyl;
or pharmaceutically acceptable salts thereof.

17. The compounds according to claim 2, wherein:
$R^1$ is —C(O)—NH-alkyl, which alkyl group is unsubstituted or substituted with a substituent selected from the group consisting of:
 —OH;
 —NH(alkyl);
 —N(alkyl)$_2$;

—NH—C(O)-alkyl;
—C(O)—NH-alkyl;
—C(O)—N(alkyl)₂;
—C(O)—NH₂;
—O-alkyl;
—S(O)-alkyl, and
—S(O)₂—NH₂;
wherein when said substituent contains an alkyl group, the alkyl group is unsubstituted or substituted with —OH;
R² is halogen;
or pharmaceutically acceptable salts thereof.

18. A compound according to claim 17, said compound selected from the group consisting of:
- 6-(2-Bromo-phenyl)-2-(4-fluoro-phenylamino)-pyrido[2,3-d]pyrimidine-7-carboxylic acid (2-dimethylamino-ethyl)-amide;
- 6-(2-Bromo-phenyl)-2-(4-fluoro-phenylamino)-pyrido[2,3-d]pyrimidine-7-carboxylic acid (2-methoxy-ethyl)-amide;
- 6-(2-Bromo-phenyl)-2-(4-fluoro-phenylamino)-pyrido[2,3-d]pyrimidine-7-carboxylic acid (3-dimethylamino-propyl)-amide;
- 6-(2-Bromo-phenyl)-2-(4-fluoro-phenylamino)-pyrido[2,3-d]pyrimidine-7-carboxylic acid (3-dimethylamino-2,2-dimethyl-propyl)-amide;
- 6-(2-Bromo-phenyl)-2-(4-fluoro-phenylamino)-pyrido[2,3-d]pyrimidine-7-carboxylic acid (2-acetylamino-ethyl)-amide;
- 6-(2-Bromo-phenyl)-2-(4-fluoro-phenylamino)-pyrido[2,3-d]pyrimidine-7-carboxylic acid (2-methylamino-ethyl)-amide;
- 6-(2-Bromo-phenyl)-2-(4-fluoro-phenylamino)-pyrido[2,3-d]pyrimidine-7-carboxylic acid carbamoylmethyl-amide;
- 6-(2-Bromo-phenyl)-2-(4-fluoro-phenylamino)-pyrido[2,3-d]pyrimidine-7-carboxylic acid (2-dimethylamino-1-methyl-ethyl)-amide;
- 6-(2-Bromo-phenyl)-2-(4-fluoro-phenylamino)-pyrido[2,3-d]pyrimidine-7-carboxylic acid methylcarbamoylmethyl-amide; and
- 6-(2-Bromo-phenyl)-2-(4-fluoro-phenylamino)-pyrido[2,3-d]pyrimidine-7-carboxylic acid (2-dimethylamino-propyl)-amide.

19. A compound according to claim 17, said compound selected from the group consisting of:
- 6-(2-Bromo-phenyl)-2-(4-fluoro-phenylamino)-pyrido[2,3-d]pyrimidine-7-carboxylic acid dimethylcarbamoyl-methyl-amide;
- 6-(2-Bromo-phenyl)-2-(4-fluoro-phenylamino)-pyrido[2,3-d]pyrimidine-7-carboxylic acid (3-methylamino-propyl)-amide;
- 6-(2-Bromo-phenyl)-2-(4-fluoro-phenylamino)-pyrido[2,3-d]pyrimidine-7-carboxylic acid (2-sulfamoyl-ethyl)-amide;
- 6-(2-Bromo-phenyl)-2-(4-fluoro-phenylamino)-pyrido[2,3-d]pyrimidine-7-carboxylic acid (2-hydroxy-ethyl)-amide;
- 6-(2-Bromo-phenyl)-2-(4-fluoro-phenylamino)-pyrido[2,3-d]pyrimidine-7-carboxylic acid (3-hydroxy-propyl)-amide;
- (S)-6-(2-Bromo-phenyl)-2-(4-fluoro-phenylamino)-pyrido[2,3-d]pyrimidine-7-carboxylic acid (2,3-dihydroxy-propyl)-amide;
- (R)-6-(2-Bromo-phenyl)-2-(4-fluoro-phenylamino)-pyrido[2,3-d]pyrimidine-7-carboxylic acid (2,3-dihydroxy-propyl)-amide;
- 6-(2-Bromo-phenyl)-2-(4-fluoro-phenylamino)-pyrido[2,3-d]pyrimidine-7-carboxylic acid (2-methanesulfinyl-ethyl)-amide; and
- 6-(2-Bromo-phenyl)-2-(4-fluoro-phenylamino)-pyrido[2,3-d]pyrimidine-7-carboxylic acid [2-(2-hydroxy-ethanesulfinyl)-ethyl]-amide.

20. The compounds according to claim 2, wherein:
R¹ is —C(O)—N(CH₃)alkyl, which alkyl group is unsubstituted or substituted with —NH(alkyl) or —N(alkyl)₂; and
R² is halogen;
or pharmaceutically acceptable salts thereof.

21. A compound according to claim 20, said compound being 6-(2-Bromo-phenyl)-2-(4-fluoro-phenylamino)-pyrido[2,3-d]pyrimidine-7-carboxylic acid (2-dimethylamino-ethyl)-methyl-amide.

22. The compounds according to claim 2, wherein:
R¹ is —C(O)—NH-alkyl, which alkyl group is substituted with
morpholin-4-yl;
pyrrolidinyl;
2-oxo-imidazolidinyl;
2-oxo-pyrrolidinyl;
1-methyl-pyrrolidinyl;
3H-imidazolyl;
1,5-dimethyl-pyrazolyl; or
—NH-pyridinyl;
R² is halogen;
or pharmaceutically acceptable salts thereof.

23. A compound according to claim 22, said compound selected from the group consisting of:
- 6-(2-Bromo-phenyl)-2-(4-fluoro-phenylamino)-pyrido[2,3-d]pyrimidine-7-carboxylic acid (2-morpholin-4-yl-ethyl)-amide;
- 6-(2-Bromo-phenyl)-2-(4-fluoro-phenylamino)-pyrido[2,3-d]pyrimidine-7-carboxylic acid [2-(2-oxo-imidazolidin-1-yl)-ethyl]-amide;
- (R)-6-(2-Bromo-phenyl)-2-(4-fluoro-phenylamino)-pyrido[2,3-d]pyrimidine-7-carboxylic acid (pyrrolidin-2-ylmethyl)-amide;
- 6-(2-Bromo-phenyl)-2-(4-fluoro-phenylamino)-pyrido[2,3-d]pyrimidine-7-carboxylic acid [3-(2-oxo-pyrrolidin-1-yl)-propyl]-amide;
- 6-(2-Bromo-phenyl)-2-(4-fluoro-phenylamino)-pyrido[2,3-d]pyrimidine-7-carboxylic acid (3-morpholin-4-yl-propyl)-amide;
- 6-(2-Bromo-phenyl)-2-(4-fluoro-phenylamino)-pyrido[2,3-d]pyrimidine-7-carboxylic acid [2-(1-methyl-pyrrolidin-2-yl)-ethyl]-amide;
- 6-(2-Bromo-phenyl)-2-(4-fluoro-phenylamino)-pyrido[2,3-d]pyrimidine-7-carboxylic acid [2-(pyridin-2-ylamino)-ethyl]-amide;
- 6-(2-Bromo-phenyl)-2-(4-fluoro-phenylamino)-pyrido[2,3-d]pyrimidine-7-carboxylic acid [2-(3H-imidazol-4-yl)-ethyl]-amide;
- 6-(2-Bromo-phenyl)-2-(4-fluoro-phenylamino)-pyrido[2,3-d]pyrimidine-7-carboxylic acid (1,5-dimethyl-1H-pyrazol-3-ylmethyl)-amide; and
- 6-(2-Bromo-phenyl)-2-(4-fluoro-phenylamino)-pyrido[2,3-d]pyrimidine-7-carboxylic acid ((S)-pyrrolidin-2-ylmethyl)-amide.

24. The compounds according to claim 2, wherein:
R¹ is —C(O)—NH-alkyl, which alkyl group is substituted with
—NH-alkyl or —N(alkyl)₂; or
—C(O)—NH-piperidin-4-yl; and
R² is morpholin-4-yl;

—S-alkyl; or
—O-alkyl, which alkyl group is substituted with —N(alkyl)2;
or pharmaceutically acceptable salts thereof.

25. A compound according to claim 24, said compound selected from the group consisting of:
   6-(2-Bromo-phenyl)-2-(3-methylsulfanyl-phenylamino)-pyrido[2,3-d]pyrimidine-7-carboxylic acid (2-dimethylamino-ethyl)-amide;
   6-(2-Bromo-phenyl)-2-(4-morpholin-4-yl-phenylamino)-pyrido[2,3-d]pyrimidine-7-carboxylic acid (2-dimethylamino-ethyl)-amide;
   6-(2-Bromo-phenyl)-2-(4-morpholin-4-yl-phenylamino)-pyrido[2,3-d]pyrimidine-7-carboxylic acid (2-methylamino-ethyl)-amide;
   6-(2-Bromo-phenyl)-2-[4-(2-diethylamino-ethoxy)-phenylamino]-pyrido[2,3-d]pyrimidine-7-carboxylic acid (2-dimethylamino-ethyl)-amide;
   6-(2-Bromo-phenyl)-2-(4-morpholin-4-yl-phenylamino)-pyrido[2,3-d]pyrimidine-7-carboxylic acid piperidin-4-ylamide; and
   6-(2-Bromo-phenyl)-2-(3-methylsulfanyl-phenylamino)-pyrido[2,3-d]pyrimidine-7-carboxylic acid (2-methylamino-ethyl)-amide.

26. The compounds according to claim 2, wherein:
   $R^1$ is —C(O)—NH-heterocyclyl;
   —C(O)—NH—NH—C(O)—NH$_2$; or
   —C(O)—NH—NH—C(O)-alkyl, which alkyl is unsubstituted or substituted with
      —NH(alkyl); or
      —N(alkyl)$_2$;
   $R^2$ is halogen;
   or pharmaceutically acceptable salts thereof.

27. A compound according to claim 26, said compound selected from the group consisting of:
   (R)-6-(2-Bromo-phenyl)-2-(4-fluoro-phenylamino)-pyrido[2,3-d]pyrimidine-7-carboxylic acid piperidin-3-ylamide;
   (S)-6-(2-Bromo-phenyl)-2-(4-fluoro-phenylamino)-pyrido[2,3-d]pyrimidine-7-carboxylic acid piperidin-3-ylamide;
   6-(2-Bromo-phenyl)-2-(4-fluoro-phenylamino)-pyrido[2,3-d]pyrimidine-7-carboxylic acid piperidin-4-ylamide;
   1-[6-(2-Bromo-phenyl)-2-(4-fluoro-phenylamino)-pyrido[2,3-d]pyrimidine-7-carbonyl]semicarbazide;
   6-(2-Bromo-phenyl)-2-(4-fluoro-phenylamino)-pyrido[2,3-d]pyrimidine-7-carboxylic acid N'-(2-dimethylamino-acetyl)-hydrazide;
   6-(2-Bromo-phenyl)-2-(4-fluoro-phenylamino)-pyrido[2,3-d]pyrimidine-7-carboxylic acid (1-methyl-piperidin-4-yl)-amide;
   (S)-6-(2-Bromo-phenyl)-2-(4-fluoro-phenylamino)-pyrido[2,3-d]pyrimidine-7-carboxylic acid pyrrolidin-3-ylamide;
   (R)-6-(2-Bromo-phenyl)-2-(4-fluoro-phenylamino)-pyrido[2,3-d]pyrimidine-7-carboxylic acid pyrrolidin-3-ylamide;
   6-(2-Bromo-phenyl)-2-(4-fluoro-phenylamino)-pyrido[2,3-d]pyrimidine-7-carboxylic acid (1-aza-bicyclo[2.2.2]oct-3-yl)-amide;
   6-(2-Bromo-phenyl)-2-(4-fluoro-phenylamino)-pyrido[2,3-d]pyrimidine-7-carboxylic acid (1H-pyrazol-3-yl)-amide;
   6-(2-Bromo-phenyl)-2-(4-fluoro-phenylamino)-pyrido[2,3-d]pyrimidine-7-carboxylic acid (2-methyl-2H-pyrazol-3-yl)-amide; and
   6-(2-Bromo-phenyl)-2-(4-fluoro-phenylamino)-pyrido[2,3-d]pyrimidine-7-carboxylic acid (4-carbamoyl-1H-pyrazol-3-yl)-amide.

28. The compounds according to claim 2, wherein:
   $R^1$ is —C(O)—NH$_2$; and
   $R^2$ is morpholin-4-yl;
      —(CH$_2$)$_m$—S(O)$_2$—NH—(alkyl);
      —(CH$_2$)$_m$—S(O)$_2$—NH$_2$;
      —O-alkyl, or
      —S(O)$_n$-alkyl,
   wherein when $R^2$ contains an alkyl group, the alkyl group is unsubstituted or substituted by
      —OH;
      —NH-alkyl; or
      —N(alkyl)$_2$;
   m is 0, 1, 2, 3, 4, 5 or 6;
   n is 0, 1 or 2;
   or pharmaceutically acceptable salts thereof.

29. A compound according to claim 28, said compound is selected from the group consisting of:
   6-(2-Bromo-phenyl)-2-(4-morpholin-4-yl-phenylamino)-pyrido[2,3-d]pyrimidine-7-carboxylic acid amide;
   6-(2-Bromo-phenyl)-2-[4-(2-diethylamino-ethoxy)-phenylamino]-pyrido[2,3-d]pyrimidine-7-carboxylic acid amide;
   6-(2-Bromo-phenyl)-2-(3-methylsulfanyl-phenylamino)-pyrido[2,3-d]pyrimidine-7-carboxylic acid amide;
   6-(2-Bromo-phenyl)-2-(4-sulfamoyl-phenylamino)-pyrido[2,3-d]pyrimidine-7-carboxylic acid amide;
   6-(2-Bromo-phenyl)-2-(3-methylsulfamoylmethyl-phenylamino)-pyrido[2,3-d]pyrimidine-7-carboxylic acid amide;
   6-(2-Bromo-phenyl)-2-[3-(2-hydroxy-ethanesulfonyl)-phenylamino]-pyrido[2,3-d]pyrimidine-7-carboxylic acid amide; and
   6-(2-Bromo-phenyl)-2-(3-methanesulfonyl-phenylamino)-pyrido[2,3-d]pyrimidine-7-carboxylic acid amide.

30. The compounds according to claim 2, wherein:
   $R^1$ is —CN; and
   $R^2$ is morpholin-4-yl;
      —S(O)$_n$-alkyl; or a group
      —O-alkyl, which alkyl group is unsubstituted or substituted by
         —OH;
         —NH-alkyl; or
         —N(alkyl)$_2$;
   n is 0, 1 or 2;
   or pharmaceutically acceptable salts thereof.

31. A compound according to claim 30, said compound selected from the group consisting of:
   6-(2-Bromo-phenyl)-2-(4-morpholin-4-yl-phenylamino)-pyrido[2,3-d]pyrimidine-7-carbonitrile; compound with trifluoro-acetic acid;
   6-(2-Bromo-phenyl)-2-(3-methanesulfonyl-phenylamino)-pyrido[2,3-d]pyrimidine-7-carbonitrile;
   6-(2-Bromo-phenyl)-2-[4-(2-diethylamino-ethoxy)-phenylamino]-pyrido[2,3-d]pyrimidine-7-carbonitrile;
   6-(2-Bromo-phenyl)-2-[4-(2-hydroxy-ethoxy)-phenylamino]-pyrido[2,3-d]pyrimidine-7-carbonitrile;
   6-(2-Bromo-phenyl)-2-[4-(2-ethylamino-ethoxy)-phenylamino]-pyrido[2,3-d]pyrimidine-7-carbonitrile;
   6-(2-Bromo-phenyl)-2-(3-methanesulfinyl-phenylamino)-pyrido[2,3-d]pyrimidine-7-carbonitrile; and
   6-(2-Bromo-phenyl)-2-[3-(2-hydroxy-ethanesulfonyl)-phenylamino]-pyrido[2,3-d]pyrimidine-7-carbonitrile.

32. The compounds according to claim 1, wherein:
R$^1$ is —C(O)—NH—(CH$_2$)$_2$—NH—S(O)$_2$—CH$_3$; and
R$^2$ is halogen;
 heterocyclyl;
 alkyl;
 —N—C(O)-alkyl;
 —N—S(O)$_2$-alkyl;
 —(CH$_2$)$_m$—S(O)$_2$—NH$_2$;
 —(CH$_2$)$_m$—S(O)$_2$—N(alkyl)$_2$;
 —(CH$_2$)$_m$—S(O)$_2$—NH—(alkyl);
 —O-alkyl; or
 —S(O)$_n$-alkyl,
 wherein when R$^2$ contains an alkyl group, the alkyl group is unsubstituted or substituted by
  —OH;
  —O-alkyl;
  —NH-alkyl; or
  —N(alkyl)$_2$;
m is 0, 1, 2, 3, 4, 5 or 6;
n is 0, 1 or 2;
or pharmaceutically acceptable salts thereof.

33. A compound according to claim 32, said compound selected from the group consisting of:
6-(2-Bromo-phenyl)-2-(4-morpholin-4-yl-phenylamino)-pyrido[2,3-d]pyrimidine-7-carboxylic acid (2-methanesulfonylamino-ethyl)-amide,
6-(2-Bromo-phenyl)-2-(3-methanesulfonylamino-phenylamino)-pyrido[2,3-d]pyrimidine-7-carboxylic acid (2-methanesulfonylamino-ethyl)-amide,
6-(2-Bromo-phenyl)-2-[4-(2-hydroxy-ethoxy)-phenylamino]-pyrido[2,3-d]pyrimidine-7-carboxylic acid (2-methanesulfonylamino-ethyl)-amide,
6-(2-Bromo-phenyl)-2-[4-(4-methyl-piperazin-1-yl)-phenylamino]-pyrido[2,3-d]pyrimidine-7-carboxylic acid (2-methanesulfonylamino-ethyl)-amide,
6-(2-Bromo-phenyl)-2-(3-methoxy-phenylamino)-pyrido[2,3-d]pyrimidine-7-carboxylic acid (2-methanesulfonylamino-ethyl)-amide,
2-(3-Acetylamino-phenylamino)-6-(2-bromo-phenyl)-pyrido[2,3-d]pyrimidine-7-carboxylic acid (2-methanesulfonylamino-ethyl)-amide,
6-(2-Bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (2-methanesulfonylamino-ethyl)-amide,
6-(2-Bromo-phenyl)-2-[3-(2-hydroxy-ethylsulfanyl)-phenylamino]-pyrido[2,3-d]pyrimidine-7-carboxylic acid (2-methanesulfonylamino-ethyl)-amide, and
6-(2-Bromo-phenyl)-2-(3-hydroxymethyl-2,3-dihydro-benzo[1,4]dioxin-6-ylamino)-pyrido[2,3-d]pyrimidine-7-carboxylic acid (2-methanesulfonyl-amino-ethyl)-amide.

34. A compound according to claim 2, said compound selected from the group consisting of:
6-(2-Bromo-phenyl)-2-(4-fluoro-phenylamino)-pyrido[2,3-d]pyrimidine-7-carboxylic acid (piperidin-2-ylmethyl)-amide,
6-(2-Bromo-phenyl)-2-(4-methanesulfinyl-phenylamino)-pyrido[2,3-d]pyrimidine-7-carboxylic acid (2-hydroxy-ethyl)-amide,
6-(2-Bromo-phenyl)-2-(3-methanesulfinyl-phenylamino)-pyrido[2,3-d]pyrimidine-7-carboxylic acid (2-hydroxy-ethyl)-amide,
6-(2-Bromo-phenyl)-2-[3-(2-hydroxy-ethylsulfamoyl)-phenylamino]-pyrido[2,3-d]pyrimidine-7-carboxylic acid (2-hydroxy-ethyl)-amide,
6-(2-Bromo-phenyl)-2-[4-(2-hydroxy-ethylsulfamoyl)-phenylamino]-pyrido[2,3-d]pyrimidine-7-carboxylic acid (2-hydroxy-ethyl)-amide,
6-(2-Bromo-phenyl)-2-(4-methanesulfinyl-phenylamino)-pyrido[2,3-d]pyrimidine-7-carboxylic acid (2-sulfamoyl-ethyl)-amide,
6-(2-Bromo-phenyl)-2-(3-methanesulfinyl-phenylamino)-pyrido[2,3-d]pyrimidine-7-carboxylic acid (2-sulfamoyl-ethyl)-amide,
6-(2-Bromo-phenyl)-2-[4-(2-hydroxy-ethoxy)-phenylamino]-pyrido[2,3-d]pyrimidine-7-carboxylic acid (2-sulfamoyl-ethyl)-amide, and
6-(2-Bromo-phenyl)-2-(3-methanesulfonyl-phenylamino)-pyrido[2,3-d]pyrimidine-7-carboxylic acid (2-sulfamoyl-ethyl)-amide.

35. The compounds according to claim 1 wherein:
R$^1$ is —C(O)—NH-alkyl, which alkyl group is substituted by
 —OH;
 —S(O)$_2$—NH$_2$; or
 pyrrolidin-2-yl; and
R$^2$ is —NH—C(O)—CH$_3$;
 —NH—S(O)$_2$—CH$_3$;
 —CH2—OH; or
 R$^2$ is fused to the phenyl ring to form a 4,4-dioxo-3,4-dihydro-2H-4lambda*6*-benzo[1,4]oxathiinyl moiety;
or pharmaceutically acceptable salts thereof.

36. A compound according to claim 35, said compound selected from the group consisting of:
6-(2-Bromo-phenyl)-2-(3-hydroxymethyl-phenylamino)-pyrido[2,3-d]pyrimidine-7-carboxylic acid (2-hydroxy-ethyl)-amide,
6-(2-Bromo-phenyl)-2-(3-hydroxymethyl-phenylamino)-pyrido[2,3-d]pyrimidine-7-carboxylic acid (2-sulfamoyl-ethyl)-amide,
6-(2-Bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (2-sulfamoyl-ethyl)-amide,
6-(2-Bromo-phenyl)-2-(4,4-dioxo-3,4-dihydro-2H-4lambda*6*-benzo[1,4]oxathiin-6-ylamino)-pyrido[2,3-d]pyrimidine-7-carboxylic acid (pyrrolidin-2-ylmethyl)-amide HCl salt,
6-(2-Bromo-phenyl)-2-(3-methanesulfonylamino-phenylamino)-pyrido[2,3-d]pyrimidine-7-carboxylic acid (pyrrolidin-2-ylmethyl)-amide HCl salt, and
2-(3-Acetylamino-phenylamino)-6-(2-bromo-phenyl)-pyrido[2,3-d]pyrimidine-7-carboxylic acid (pyrrolidin-2-ylmethyl)-amide HCl salt.

37. A process for the manufacture of the compound according to claim 1, comprising:
(a) converting the sulfide group in the compounds of the general formula (II)

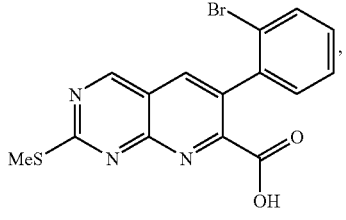

formula (II)

into the corresponding sulfoxide group, which sulfoxide group is (b) substituted by the respective anilines of formula (II-A)

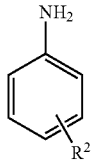

formula (II-A)

wherein R² has the meaning given in claim 1, to give the compound of the general formula (IV)

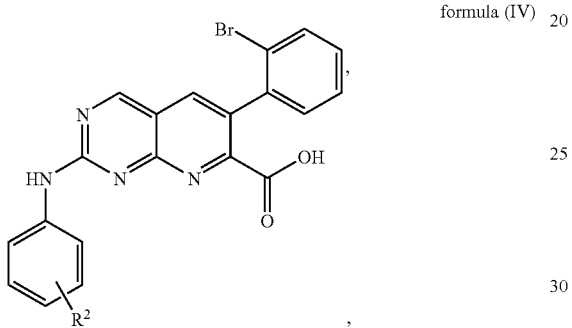

formula (IV)

(c) converting the —COOH group in formula (IV) into an amide derivative of formula (I).

38. The process according to claim 37, further comprising:
(d) converting the primary amide derivative obtained from (c) into its corresponding 7-carbonitril derivative of formula (I).

39. The process according to claim 38, further comprising:
(e) converting said compound of the general formula (I), obtained from (c) or (d), into a pharmaceutically acceptable salt.

40. A method for the treatment of colon cancer comprising administering, to a patient in need thereof, a therapeutically effective amount of a compound according to formula I:

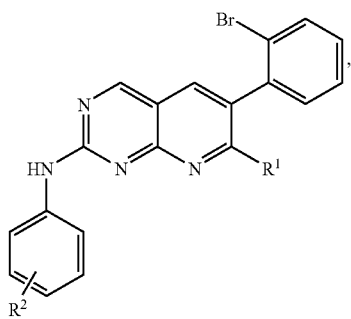

(formula I)

wherein:
R¹ is —C(O)—NH-alkyl or —C(O)—N(alkyl)₂, which alkyl groups are unsubstituted or substituted with at least one substituent selected from the group consisting of:
—OH;
—NH(alkyl);
—N(alkyl)₂;
—NH—C(O)-alkyl;
—C(O)—NH-alkyl;
—C(O)—N(alkyl)₂;
—C(O)—NH₂;
—O-alkyl;
-heterocyclyl;
—NH-heterocyclyl;
—NH—S(O)₂-alkyl;
—S(O)₂—NH₂; and
—S(O)-alkyl,
wherein when said at least one substituent contains an alkyl group, the alkyl group is unsubstituted or substituted with —OH;
or a group
—CN;
—C(O)—NH₂;
—C(O)—NH-heterocyclyl;
—C(O)—NH—NH—C(O)—NH₂; or
—C(O)—NH—NH—C(O)-alkyl, which alkyl is unsubstituted or substituted with
—NH(alkyl); or
—N(alkyl)₂; and
R² is halogen;
heterocyclyl;
alkyl;
—NH—C(O)-alkyl;
—NH—S(O)₂-alkyl;
—(CH₂)ₘ—S(O)₂—NH₂;
—(CH₂)ₘ—S(O)₂—N(alkyl)₂;
—(CH₂)ₘ—S(O)₂—NH—(alkyl);
—O-alkyl; or
—S(O)ₙ-alkyl,
wherein when R² contains an alkyl group, the alkyl group is unsubstituted or substituted by
—OH;
—O-alkyl;
—NH-alkyl; or
—N(alkyl)₂;
m is 0, 1, 2, 3, 4, 5 or 6;
n is 0, 1 or 2;
or pharmaceutically acceptable salts thereof.

41. A pharmaceutical composition comprising a compound of formula I:

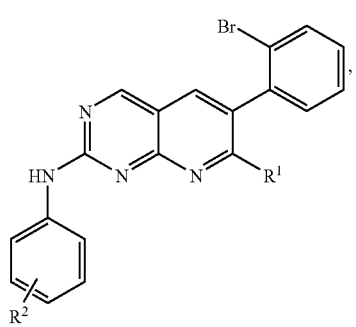

(formula I)

wherein:
$R^1$ is —C(O)—NH-alkyl or —C(O)—N(alkyl)$_2$, which alkyl groups are unsubstituted or substituted with at least one substituent selected from the group consisting of:
—OH;
—NH(alkyl);
—N(alkyl)$_2$;
—NH—C(O)-alkyl;
—C(O)—NH-alkyl;
—C(O)—N(alkyl)$_2$;
—C(O)—NH$_2$;
—O-alkyl;
-heterocyclyl;
—NH-heterocyclyl;
—NH—S(O)$_2$-alkyl;
—S(O)$_2$—NH$_2$; and
—S(O)-alkyl,
wherein when said at least one substituent contains an alkyl group, the alkyl group is unsubstituted or substituted with —OH;
or a group
—CN;
—C(O)—NH$_2$;
—C(O)—NH-heterocyclyl;
—C(O)—NH—NH—C(O)—NH$_2$; or
—C(O)—NH—NH—C(O)-alkyl, which alkyl is unsubstituted or substituted with
—NH(alkyl); or
—N(alkyl)$_2$; and
$R^2$ is halogen;
heterocyclyl;
alkyl;
—NH—C(O)-alkyl;
—NH—S(O)$_2$-alkyl;
—(CH$_2$)$_m$—S(O)$_2$—NH$_2$;
—(CH$_2$)$_m$—S(O)$_2$—N(alkyl)$_2$;
—(CH$_2$)$_m$—S(O)$_2$—NH—(alkyl);
—O-alkyl; or
—S(O)$_n$-alkyl,
wherein when R2 contains an alkyl group, the alkyl group is unsubstituted or substituted by
—OH;
—O-alkyl;
—NH-alkyl; or
—N(alkyl)$_2$;
m is 0, 1, 2, 3, 4, 5 or 6;
n is 0, 1 or 2;
or pharmaceutically acceptable salts thereof.

* * * * *

```
                        SEQUENCE LISTING

<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Glu Glu Glu Ile Tyr Gly Glu Phe Glu Ala Lys Lys Lys Lys
 1               5                  10                  15

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Aminocaprylic acid

<400> SEQUENCE: 2

Gly Xaa Ala Glu Glu Glu Ile Tyr Gly Glu Phe Glu Ala Lys Lys Lys
 1               5                  10                  15

Lys
```